United States Patent
Stern et al.

(10) Patent No.: US 10,303,922 B2
(45) Date of Patent: *May 28, 2019

(54) METHODS AND DEVICES FOR READING MICROARRAYS

(71) Applicant: Affymetrix, Inc., Carlsbad, CA (US)

(72) Inventors: David Stern, Mountain View, CA (US); Chuan Gao, Sunnyvale, CA (US); Melvin Yamamoto, Fremont, CA (US); Devin Nguyen, San Jose, CA (US)

(73) Assignee: Affymetrix, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/993,512

(22) Filed: May 30, 2018

(65) Prior Publication Data
US 2018/0341802 A1    Nov. 29, 2018

Related U.S. Application Data

(62) Division of application No. 15/687,400, filed on Aug. 25, 2017, now Pat. No. 10,019,620, which is a
(Continued)

(51) Int. Cl.
*G06K 9/00* (2006.01)
*G01N 21/64* (2006.01)
(Continued)

(52) U.S. Cl.
CPC ..... *G06K 9/00134* (2013.01); *G01N 21/6452* (2013.01); *G02B 21/008* (2013.01);
(Continued)

(58) Field of Classification Search
CPC ........... G06K 9/00134; G01N 21/6452; G02B 21/361; G02B 21/008; G02B 21/16; G02B 21/0076; Y10T 29/49826
(Continued)

(56) References Cited

U.S. PATENT DOCUMENTS 4,185,274 A    1/1980 Giallorenzi
4,410,799 A    10/1983 Okamoto
(Continued)

FOREIGN PATENT DOCUMENTS

EP    0 957 642 A2    11/1999
EP    0 990 896 A2    4/2000
(Continued)

OTHER PUBLICATIONS

U.S. Appl. No. 10/623,883, filed Jul. 21, 2003, Lobban et al.
(Continued)

*Primary Examiner* — Amandeep Saini
(74) *Attorney, Agent, or Firm* — Mauriel Kapouytian Woods LLP; Andrew A. Noble; Michael Mauriel

(57) ABSTRACT

In one embodiment of the invention, a method to image a probe array is described that includes focusing on a plurality of fiducials on a surface of an array. The method utilizes obtaining the best z position of the fiducials and using a surface fitting algorithm to produce a surface fit profile. One or more surface non-flatness parameters can be adjusted to improve the flatness image of the array surface to be imaged.

28 Claims, 9 Drawing Sheets

Related U.S. Application Data division of application No. 12/780,825, filed on May 14, 2010, now Pat. No. 9,767,342.

(60) Provisional application No. 61/180,789, filed on May 22, 2009.

(51) Int. Cl.
*G02B 21/00* (2006.01)
*G02B 21/16* (2006.01)
*G02B 21/36* (2006.01)

(52) U.S. Cl.
CPC ......... *G02B 21/0076* (2013.01); *G02B 21/16* (2013.01); *G02B 21/361* (2013.01); *Y10T 29/49826* (2015.01)

(58) Field of Classification Search
USPC ........................................................ 382/100
See application file for complete search history.

(56) References Cited

U.S. PATENT DOCUMENTS

| | | | |
|---|---|---|---|
| 4,665,034 A | 5/1987 | Chandler | |
| 4,758,727 A | 7/1988 | Tomei et al. | |
| 4,829,010 A | 5/1989 | Chang | |
| 4,855,597 A | 8/1989 | Shimura | |
| 4,859,419 A | 8/1989 | Marks et al. | |
| 4,877,966 A | 10/1989 | Tomei et al. | |
| 4,890,247 A | 12/1989 | Sarrine et al. | |
| 5,032,720 A | 7/1991 | White | |
| 5,093,978 A | 3/1992 | Binder | |
| 5,102,177 A | 4/1992 | Dreisig et al. | |
| 5,104,808 A | 4/1992 | Laska et al. | |
| 5,121,138 A | 6/1992 | Schermer et al. | |
| 5,143,854 A | 9/1992 | Pirrung et al. | |
| 5,154,888 A | 10/1992 | Zander et al. | |
| 5,229,297 A | 7/1993 | Schnipelsky et al. | |
| 5,230,866 A | 7/1993 | Shartle et al. | |
| 5,233,844 A | 8/1993 | Knippscheer et al. | |
| 5,258,781 A | 11/1993 | John | |
| 5,279,721 A | 1/1994 | Schmid | |
| 5,288,463 A | 2/1994 | Chemelli | |
| 5,296,195 A | 3/1994 | Pang et al. | |
| 5,302,824 A | 4/1994 | Prager | |
| 5,384,261 A | 1/1995 | Winkler et al. | |
| 5,388,945 A | 2/1995 | Garric et al. | |
| 5,422,271 A | 6/1995 | Chen et al. | |
| 5,424,186 A | 6/1995 | Fodor et al. | |
| 5,434,595 A | 7/1995 | Macaulay | |
| 5,436,129 A | 7/1995 | Stapleton | |
| 5,459,325 A | 10/1995 | Hueton et al. | |
| 5,486,335 A | 1/1996 | Wilding et al. | |
| 5,489,678 A | 2/1996 | Fodor et al. | |
| 5,500,187 A | 3/1996 | Deoms et al. | |
| 5,528,050 A | 6/1996 | Miller et al. | |
| 5,538,613 A | 7/1996 | Brumley et al. | |
| 5,543,329 A | 8/1996 | Bedell | |
| 5,578,832 A | 11/1996 | Trulson et al. | |
| 5,585,639 A | 12/1996 | Dorsel et al. | |
| 5,587,128 A | 12/1996 | Wilding et al. | |
| 5,593,838 A | 1/1997 | Zanzucchi et al. | |
| 5,593,839 A | 1/1997 | Hubbell et al. | |
| 5,595,908 A | 1/1997 | Fawcett et al. | |
| 5,599,504 A | 2/1997 | Hosoi et al. | |
| 5,627,041 A | 5/1997 | Shartle | |
| 5,631,734 A | 5/1997 | Stern et al. | |
| 5,635,358 A | 6/1997 | Wilding et al. | |
| 5,637,469 A | 6/1997 | Wilding et al. | |
| 5,652,149 A | 7/1997 | Mileaf et al. | |
| 5,658,802 A | 8/1997 | Hayes et al. | |
| 5,674,743 A | 10/1997 | Ulmer | |
| 5,675,700 A | 10/1997 | Atwood et al. | |
| 5,683,916 A | 11/1997 | Goffe et al. | |
| 5,689,110 A | 11/1997 | Dietz et al. | |
| 5,698,450 A | 12/1997 | Ringrose et al. | |
| 5,716,825 A | 2/1998 | Hancock et al. | |
| 5,721,435 A | 2/1998 | Troll | |
| 5,726,010 A | 3/1998 | Clark | |
| 5,726,013 A | 3/1998 | Clark | |
| 5,763,870 A | 6/1998 | Sadler et al. | |
| 5,822,211 A * | 10/1998 | Barenboim | B23K 26/067 700/166 |
| 5,834,758 A | 11/1998 | Trulson et al. | |
| 5,895,915 A | 4/1999 | DeWeerd et al. | |
| 5,936,324 A | 8/1999 | Montagu | |
| 5,945,334 A | 8/1999 | Besemer et al. | |
| 5,954,804 A | 9/1999 | Farmwald et al. | |
| 5,962,834 A | 10/1999 | Markman | |
| 5,981,956 A | 11/1999 | Stern | |
| 5,984,474 A | 11/1999 | Schweitzer et al. | |
| 6,025,601 A | 2/2000 | Trulson et al. | |
| 6,036,781 A | 3/2000 | Ahn et al. | |
| 6,042,324 A | 3/2000 | Aggarwal et al. | |
| 6,066,448 A | 5/2000 | Wohlstadter et al. | |
| 6,068,437 A | 5/2000 | Boje et al. | |
| 6,072,417 A | 6/2000 | Staton | |
| 6,073,366 A | 6/2000 | Aswad | |
| 6,075,613 A | 6/2000 | Schermer et al. | |
| 6,078,390 A | 6/2000 | Bengtsson | |
| 6,090,545 A | 7/2000 | Wohlstadter et al. | |
| 6,090,555 A | 7/2000 | Fiekowsky et al. | |
| 6,097,025 A | 8/2000 | Modlin et al. | |
| 6,130,440 A | 10/2000 | Ogura | |
| 6,141,096 A | 10/2000 | Stern et al. | |
| 6,143,152 A | 11/2000 | Simpson et al. | |
| 6,166,367 A | 12/2000 | Cho | |
| 6,166,385 A | 12/2000 | Webb et al. | |
| 6,169,289 B1 | 1/2001 | White et al. | |
| 6,171,793 B1 | 1/2001 | Phillips et al. | |
| 6,185,030 B1 | 2/2001 | Overbeck | |
| 6,191,802 B1 | 2/2001 | Kessler | |
| 6,201,639 B1 | 3/2001 | Overbeck | |
| 6,209,983 B1 | 4/2001 | Osborne et al. | |
| 6,211,913 B1 | 4/2001 | Hansen et al. | |
| 6,211,989 B1 | 4/2001 | Wulf et al. | |
| 6,218,803 B1 | 4/2001 | Montagu et al. | |
| 6,225,625 B1 | 5/2001 | Pirrung et al. | |
| 6,229,607 B1 | 5/2001 | Shirai et al. | |
| 6,245,507 B1 | 6/2001 | Bogdanov | |
| 6,309,601 B1 | 10/2001 | Juncosa et al. | |
| 6,312,914 B1 | 11/2001 | Kardos et al. | |
| 6,347,259 B1 | 2/2002 | Goldenberg et al. | |
| 6,352,861 B1 | 3/2002 | Copeland et al. | |
| 6,353,475 B1 | 3/2002 | Jensen et al. | |
| 6,362,004 B1 | 3/2002 | Noblett | |
| 6,371,370 B2 | 4/2002 | Sadler et al. | |
| 6,395,554 B1 | 5/2002 | Regan et al. | |
| 6,490,533 B2 | 12/2002 | Weiner et al. | |
| 6,507,426 B2 | 1/2003 | Makino | |
| 6,511,277 B1 | 1/2003 | Norris et al. | |
| 6,514,768 B1 | 2/2003 | Guire et al. | |
| 6,518,556 B2 | 2/2003 | Staton et al. | |
| 6,531,864 B2 | 3/2003 | Montagu | |
| 6,537,801 B1 | 3/2003 | Ida et al. | |
| 6,545,758 B1 | 4/2003 | Sandstrom | |
| 6,555,802 B2 | 4/2003 | Osipchuk et al. | |
| 6,583,424 B2 | 6/2003 | Staton et al. | |
| 6,591,196 B1 | 7/2003 | Yakhini et al. | |
| 6,592,036 B2 | 7/2003 | Sadler et al. | |
| 6,687,395 B1 | 2/2004 | Dietz et al. | |
| 6,693,269 B2 | 2/2004 | Shimizu et al. | |
| 6,740,871 B1 | 5/2004 | Staton et al. | |
| 6,788,414 B1 | 9/2004 | Yeung et al. | |
| 6,789,040 B2 | 9/2004 | Kaushikkar | |
| 6,813,567 B2 | 11/2004 | Weiner et al. | |
| 6,879,915 B2 | 4/2005 | Cattell | |
| 6,881,579 B2 | 4/2005 | Hilson et al. | |
| 6,914,229 B2 | 7/2005 | Corson et al. | |
| 6,965,704 B2 | 11/2005 | Kaushikkar et al. | |
| 6,993,173 B2 | 1/2006 | Zuzan et al. | |
| 7,006,927 B2 | 2/2006 | Yakhini et al. | |
| 7,023,369 B2 | 4/2006 | Bocko et al. | |
| 7,033,754 B2 | 4/2006 | Chee et al. | |

(56) References Cited

U.S. PATENT DOCUMENTS

| | | |
|---|---|---|
| 7,045,756 B2 | 5/2006 | Kinney et al. |
| 7,062,091 B2 | 6/2006 | Brown et al. |
| 7,067,819 B2 | 6/2006 | Janik |
| 7,125,523 B2 | 10/2006 | Sillman |
| 7,135,143 B2 | 11/2006 | Abbott et al. |
| 7,145,645 B2 | 12/2006 | Blumenfeld et al. |
| 7,222,025 B2 | 5/2007 | Weiner et al. |
| 7,317,415 B2 | 1/2008 | Kaiser et al. |
| 7,324,677 B2 | 1/2008 | Minor |
| 7,359,142 B2 | 4/2008 | Heineman et al. |
| 7,406,391 B2 | 7/2008 | Miles |
| 7,689,022 B2 | 3/2010 | Weiner et al. |
| 7,871,812 B2 | 1/2011 | Weiner et al. |
| 9,767,342 B2 | 9/2017 | Stern et al. |
| 10,019,620 B2 | 7/2018 | Stern et al. |
| 2003/0001072 A1 | 1/2003 | Dorsel et al. |
| 2003/0152255 A1 | 8/2003 | Kira et al. |
| 2004/0224332 A1 | 11/2004 | Loney |
| 2005/0063806 A1 | 3/2005 | Norris et al. |
| 2006/0253035 A1* | 11/2006 | Stern .................. G01N 21/6428 600/476 |
| 2008/0101668 A1 | 5/2008 | Boyden et al. |
| 2008/0101688 A1* | 5/2008 | Quadling ........... G01B 11/2527 382/154 |
| 2010/0142850 A1 | 6/2010 | Weiner et al. |

FOREIGN PATENT DOCUMENTS

| | | |
|---|---|---|
| EP | 1 031 812 A2 | 8/2000 |
| EP | 1 186 673 A2 | 3/2002 |
| EP | 0 746 865 B1 | 3/2003 |
| EP | 0 864 858 B1 | 4/2010 |
| EP | 1 345 026 B1 | 5/2010 |
| JP | 2000125174 A | 4/2000 |
| JP | 2000151971 A | 5/2000 |
| JP | 2000261618 A | 9/2000 |
| WO | 89/10977 A1 | 11/1989 |
| WO | 89/11548 A1 | 11/1989 |
| WO | 95/33846 A1 | 12/1995 |
| WO | 98/35233 A1 | 8/1998 |
| WO | 99/47964 A1 | 9/1999 |
| WO | 01/35080 A1 | 5/2001 |
| WO | 01/35099 | 5/2001 |
| WO | 03/100474 A2 | 12/2003 |

OTHER PUBLICATIONS

"Agilent Technologies announces launch of next-generation fully automated DNA microarray scanner," Agilent Technologies, Inc., Jun. 25, 2001, 2 pages.

Pellizzari et al., "Image registration based on anatomical surface matching," Interactive Image-Guided Neurosurgery, American Association of Neurological Surgeons (1993), pp. 47-62.

Bai et al., "Evaluation of cortical current density imaging methods using intracranial electrocorticograms and functional MRI," Neuroimage, vol. 35, Issue 2, Apr. 1, 2007, pp. 598-608.

Chikomo et al., "Adaptive Building Model Reconstruction From Airborne Lidar and Optical Imagery," 5 pages.

Epstein et al., "High-density, microsphere-based fiber optic DNA microarrays," Biosensors and Bioelectronics, vol. 18, Issue 5-6, May 2003, pp. 541-546.

Ma et al., "Parameterization of randomly measured points for least squares fitting of B-spline curves and surfaces," Computer-Aided Design, vol. 27, No. 9, Sep. 1995, pp. 663-675.

Montagu et al., "Fluorescence Array Scanner Employing a Flying Objective," Journal of the Association for Laboratory Automation, vol. 4, No. 1, 1999, pp. 40-43.

\* cited by examiner

METHODS AND DEVICES FOR READING MICROARRAYS

RELATED APPLICATIONS

This application is a division of U.S. application Ser. No. 15/687,400, filed Aug. 25, 2017, which is a division of U.S. application Ser. No. 12/780,825, filed May 14, 2010, which claims priority to U.S. Provisional Application No. 61/180,789, filed May 22, 2009. The entire contents of these applications are hereby incorporated herein by reference.

BACKGROUND OF THE INVENTION

Systems and methods for examining biological material are provided. In particular, provided is the acquisition of images by exposing biological probe arrays comprising probe features to an excitation light and detecting the responsive emitted light from fluorescent labels associated with target molecule hybridized to the probes of one or more probe features.

Synthesized nucleic acid probe arrays, such as Affymetrix GENECHIP® probe arrays, and spotted probe arrays, have been used to generate unprecedented amounts of information about biological systems. For example, the GENECHIP® Human Genome U133 Plus 2.0 Array for expression applications available from Affymetrix, Inc. of Santa Clara, Calif., is comprised of one microarray containing 1,300,000 oligonucleotide features covering more than 47,000 transcripts and variants that include 38,500 well characterized human genes. Similarly, the GENECHIP® Mapping 500K Array Set for genotyping applications available from Affymetrix, Inc. of Santa Clara, Calif., is comprised of two arrays, each capable of genotyping on average 250,000 SNPs. Analysis of expression or genotyping data from such microarrays may lead to the development of new drugs and new diagnostic tools.

SUMMARY OF THE INVENTION

A method to image a probe array is provided according to an embodiment of the invention. The method includes focusing on a plurality of fiducials on a surface of an array. A plurality of images is taken at a plurality of various z positions. The sharpness at each z position is determined by employing various software program embodiments. A best z position is chosen by comparing the images of the various z positions and choosing the sharpest image. The above steps are repeated until the best z position of each fiducial on the probe array is determined. The measurement data are transmitted to a computer, wherein the computer includes a software program having one or more surface fitting algorithms. A surface fit profile is calculated on the computer employing the surface fitting algorithm(s) and using the transmitted measurement data. Based on the calculations of the surface fit profile, one or more surface non-flatness parameters can be adjusted to improve the image flatness of the surface image of the probe array. The steps above can be repeated to obtain an image of the probe array.

In alternate embodiments, the imaging method may include a number of fiducials, for example, at least 4, at least 5 and at least 9 fiducials. The surface fitting algorithm may include, but does not necessarily have to include, a least square, sub-plane surface fit, and B spline surface fit.

In another embodiment, the imaging method includes the array on a tilt stage which is discussed later in the application. Focusing the array includes tilting the tilt stage so that the array surface is made parallel to a focal plane of a microscope objective.

In a further embodiment, the surface non-flatness parameters may include one or more of an array tilt, stage movement effect and optical parameters. In a further embodiment, a focal plane may be adjusted by moving a lens.

In an additional embodiment, the provided is a method of manufacturing a filter slider for reading a biological array. A linear slide and a plurality of filter sets are provided in this embodiment. The filter sets are mounted in a fixture that is mounted on a linear slide. A linear actuator is also provided and coupled to the linear slide such that the filer slider functions properly even if the linear actuator is misaligned relative to the linear slide. The linear actuator comprises a motor. In an alternate embodiment, the motor is a stepping motor and a blade slider, such as a steel shim stock coupled to the linear actuator with the filter slider.

BRIEF DESCRIPTION OF THE FIGURES

FIG. 4A illustrates a fluorescence image of a sub-array. FIG. 4B illustrates an image of a sub-array showing the spatial relationship between chrome features and fluorescent features; FIG. 5A shows the location of the 4 points on a wafer. FIG. 5B shows a scanned image of the results from the 4 points array surface analysis and FIG. 5C shows the comparison of the array surface characterization between the "calculated" surface and the actual surface.

FIG. 6A shows the location of the 5 points on an array. FIG. 6B shows a scanned image of the results from the 5 points array surface and FIG. 6C shows the comparison of the array surface characterization between the "calculated" surface and the actual surface.

FIG. 7A shows the location of the 9 points on an array. FIG. 7B shows a scanned image of the results from the 9 points array surface. FIGS. 7C, 7D, and 7E show the comparisons of the array surface characterization between the "calculated" surface using various fitting algorithms and the actual surface.

DETAILED DESCRIPTION OF THE INVENTION

Figure 1:
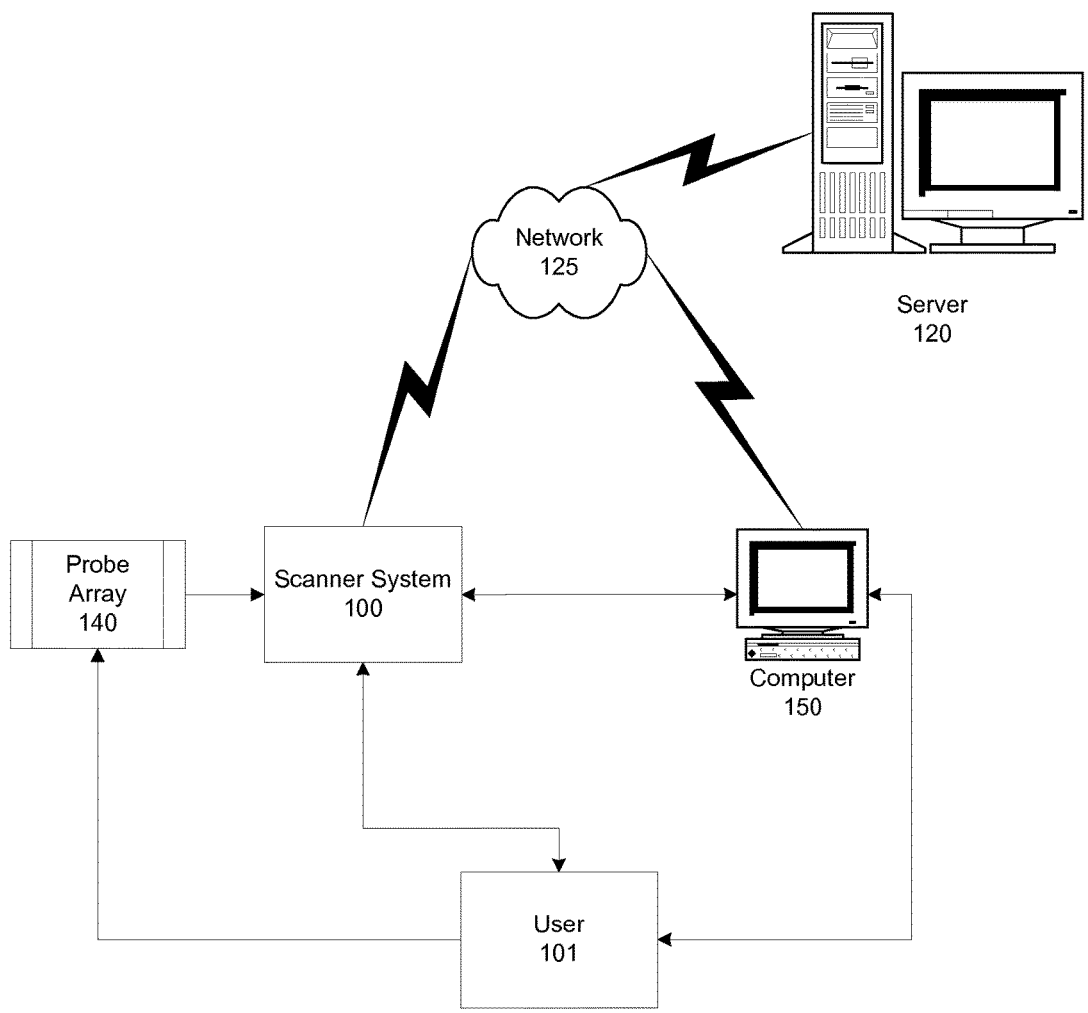
FIG. 1 illustrates a functional block diagram of one embodiment of a scanner system enabled to scan a probe array and computer system for image acquisition and analysis.

Reference will now be made in detail to exemplary embodiments of the invention. While the invention will be described in conjunction with the exemplary embodiments, it will be understood that they are not intended to limit the invention to these embodiments. On the contrary, the invention is intended to encompass alternatives, modifications and equivalents, which may be included within the spirit and scope of the invention.

The invention relates to diverse fields impacted by the nature of molecular interaction, including chemistry, biology, medicine and diagnostics. Methods disclosed herein are advantageous in fields, such as those in which genetic information is required quickly, as in clinical diagnostic laboratories or in large-scale undertakings such as the Human Genome Project.

The present invention has many embodiments and relies on many patents, applications and other references for details known to those of the art. Therefore, when a patent, application, or other reference is cited or repeated below, it should be understood that the entire disclosure of the document cited is incorporated by reference in its entirety for all purposes as well as for the proposition that is recited. All documents, i.e., publications and patent applications, cited in this disclosure, including the foregoing, are incorporated herein by reference in their entireties for all purposes to the same extent as if each of the individual documents were specifically and individually indicated to be so incorporated herein by reference in its entirety.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including, but not limited to, mammals, plants, bacteria, or cells derived from any of the above.

Throughout this disclosure, various aspects of this invention can be presented in a range format. It should be understood that when a description is provided in range format, this is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of one of skill in the art. Such conventional techniques include polymer array synthesis, hybridization, ligation, and detection of hybridization using a detectable label. Specific illustrations of suitable techniques are provided by reference to the examples hereinbelow. However, other equivalent conventional procedures may also be employed. Such conventional techniques and descriptions may be found in standard laboratory manuals, such as *Genome Analysis: A Laboratory Manual Series* (*Vols. I-IV*), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995), *Biochemistry*, 4th Ed., Freeman, New York, Gait, *Oligonucleotide Synthesis: A Practical Approach*, (1984), IRL Press, London, Nelson and Cox (2000), Lehninger, *Principles of Biochemistry*, $3^{rd}$ Ed., W.H. Freeman Pub., New York, N.Y., and Berg et al. (2002), *Biochemistry*, $5^{th}$ Ed., W.H. Freeman Pub., New York, N.Y., all of which are herein incorporated in their entirety by reference for all purposes.

The present invention may employ solid substrates, including arrays in some embodiments. Methods and techniques applicable to polymer (including protein) array synthesis have been described in U.S. patent application Ser. No. 09/536,841 (abandoned), WO Application Serial No. 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, and in PCT Application Serial Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include, but are not limited to, those that are commercially available from Affymetrix (Santa Clara, Calif.) under the brand name GENECHIP®. Example arrays are shown on the website at Affymetrix.com.

The present invention contemplates many uses for polymers attached to solid substrates. These uses include, but are not limited to, gene expression monitoring, profiling, library screening, genotyping and diagnostics. Methods of gene expression monitoring and profiling are described in U.S. Pat. Nos. 5,800,992, 6,013,449, 6,020,135, 6,033,860, 6,040,138, 6,177,248 and 6,309,822. Genotyping methods, and uses thereof, are disclosed in U.S. patent application Ser. No. 10/442,021 (abandoned) and U.S. Pat. Nos. 5,856,092, 6,300,063, 5,858,659, 6,284,460, 6,361,947, 6,368,799, 6,333,179, and 6,872,529. Other uses are described in U.S. Pat. Nos. 5,871,928, 5,902,723, 6,045,996, 5,541,061, and 6,197,506.

The present invention also contemplates sample preparation methods in certain embodiments. Prior to, or concurrent with, genotyping, the genomic sample may be amplified by a variety of mechanisms, some of which may employ PCR. (See, for example, *PCR Technology: Principles and Applications for DNA Amplification*, Ed. H. A. Erlich, Freeman Press, NY, N.Y., 1992; *PCR Protocols: A Guide to Methods and Applications*, Eds. Innis, et al., Academic Press, San Diego, Calif., 1990; Mattila et al., *Nucleic Acids Res.*, 19:4967, 1991; Eckert et al., *PCR Methods and Applications*, 1:17, 1991; PCR, Eds. McPherson et al., IRL Press, Oxford, 1991; and U.S. Pat. Nos. 4,683,202, 4,683,195, 4,800,159 4,965,188, and 5,333,675, each of which is incorporated herein by reference in their entireties for all purposes. The sample may also be amplified on the array. (See, for example, U.S. Pat. No. 6,300,070 and U.S. patent application Ser. No. 09/513,300 (abandoned), all of which are incorporated herein by reference).

Other suitable amplification methods include the ligase chain reaction (LCR) (see, for example, Wu and Wallace, *Genomics*, 4:560 (1989), Landegren et al., *Science*, 241:

1077 (1988) and Barringer et al., *Gene*, 89:117 (1990)), transcription amplification (Kwoh et al., *Proc. Natl. Acad. Sci. USA*, 86:1173 (1989) and WO 88/10315), self-sustained sequence replication (Guatelli et al., *Proc. Nat. Acad. Sci. USA*, 87:1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) and nucleic acid based sequence amplification (NABSA). (See also, U.S. Pat. Nos. 5,409,818, 5,554,517, and 6,063,603, each of which is incorporated herein by reference). Other amplification methods that may be used are described in, for instance, U.S. Pat. Nos. 6,582,938, 5,242,794, 5,494,810, and 4,988,617, each of which is incorporated herein by reference.

Additional methods of sample preparation and techniques for reducing the complexity of a nucleic sample are described in Dong et al., *Genome Research*, 11:1418 (2001), U.S. Pat. Nos. 6,361,947, 6,391,592, 6,632,611, 6,872,529 and 6,958,225, and in U.S. patent application Ser. No. 09/916,135 (abandoned).

Methods for conducting polynucleotide hybridization assays have been well developed in the art. Hybridization assay procedures and conditions will vary depending on the application and are selected in accordance with known general binding methods, including those referred to in Maniatis et al., Molecular Cloning: *A Laboratory Manual*, 2$^{nd}$ Ed., Cold Spring Harbor, N.Y., (1989); Berger and Kimmel, *Methods in Enzymology, Guide to Molecular Cloning Techniques*, Vol. 152, Academic Press, Inc., San Diego, Calif. (1987); Young and Davism, *Proc. Nat'l. Acad. Sci.*, 80:1194 (1983). Methods and apparatus for performing repeated and controlled hybridization reactions have been described in, for example, U.S. Pat. Nos. 5,871,928, 5,874,219, 6,045,996, 6,386,749, and 6,391,623 each of which are incorporated herein by reference.

The present invention also contemplates signal detection of hybridization between ligands in certain embodiments. (See, U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625, U.S. patent application Ser. No. 10/389,194 (U.S. Patent Application Publication No. 2004/0012676) and PCT Application PCT/US99/06097 (published as WO 99/47964), each of which is hereby incorporated by reference in its entirety for all purposes).

The practice of the present invention may also employ conventional biology methods, software and systems. Computer software products of the invention typically include, for instance, computer readable medium having computer-executable instructions for performing the logic steps of the method of the invention. Suitable computer readable medium include, but are not limited to, a floppy disk, CD-ROM/DVD/DVD-ROM, hard-disk drive, flash memory, ROM/RAM, magnetic tapes, etc. The computer executable instructions may be written in a suitable computer language or combination of several computer languages. Basic computational biology methods which may be employed in the present invention are described in, for example, Setubal and Meidanis et al., *Introduction to Computational Biology Methods*, PWS Publishing Company, Boston, (1997); Salzberg, Searles, Kasif, (Ed.), *Computational Methods in Molecular Biology*, Elsevier, Amsterdam, (1998); Rashidi and Buehler, *Bioinformatics Basics: Application in Biological Science and Medicine*, CRC Press, London, (2000); and Ouelette and Bzevanis *Bioinformatics: A Practical Guide for Analysis of Gene and Proteins*, Wiley & Sons, Inc., 2$^{nd}$ ed., (2001). (See also, U.S. Pat. No. 6,420,108).

The present invention may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170).

Additionally, the present invention encompasses embodiments that may include methods for providing genetic information over networks such as the internet, as disclosed in, for instance, U.S. patent application Ser. No. 10/197,621 (U.S. Patent Application Publication No. 20030097222), Ser. No. 10/063,559 (U.S. Patent Application Publication No. 20020183936, abandoned), Ser. No. 10/065,856 (U.S. Patent Application Publication No. 20030100995, abandoned), Ser. No. 10/065,868 (U.S. Patent Application Publication No. 20030120432, abandoned), Ser. No. 10/328,818 (U.S. Patent Application Publication No. 20040002818, abandoned), Ser. No. 10/328,872 (U.S. Patent Application Publication No. 20040126840, abandoned), Ser. No. 10/423,403 (U.S. Patent Application Publication No. 20040049354, abandoned), and 60/482,389 (expired).

A. Definitions

The term "array" as used herein refers to an intentionally created collection of molecules which can be prepared either synthetically or biosynthetically. The molecules in the array can be identical or different from each other. The array can assume a variety of formats, including, but not limited to, libraries of soluble molecules, and libraries of compounds tethered to resin beads, silica chips, or other solid supports. An array may include polymers of a give length having all possible monomer sequences made up of a specific bases set of monomers, or a specific subset of such an array. In other cases as array may be formed from inorganic materials (See Schultz et al PCT application WO 96/11878.).

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers which can be ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "edge" as used herein refers to a boundary between two features on a surface of a substrate. The sharpness of this edge, in terms of reduced bleed over from one feature to another, is termed the "contrast" between the two features.

The term "feature" as used herein refers to a selected region on a surface of a substrate in which a given polymer sequence is contained. Thus, where an array contains, e.g., 100,000 different positionally distinct polymer sequences on a single substrate, there will be 100,000 features.

The term "Functional group" as used herein refers to a reactive chemical moiety present on a given monomer, polymer or substrate surface. Examples of functional groups include, e.g., the 3' and 5' hydroxyl groups of nucleotides and nucleosides, as well as the reactive groups on the nucleobases of the nucleic acid monomers, e.g., the exocyclic amine group of guanosine, as well as amino and carboxyl groups on amino acid monomers.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotype" as used herein refers to the genetic information an individual carries at one or more positions in the genome. A genotype may refer to the information present at a single polymorphism, for example, a single SNP. For example, if a SNP is biallelic and can be either an A or a C then if an individual is homozygous for A at that position the genotype of the SNP is homozygous A or AA. Genotype may also refer to the information present at a plurality of polymorphic positions.

The term "Hardy-Weinberg equilibrium" (HWE) as used herein refers to the principle that an allele that when homozygous leads to a disorder that prevents the individual from reproducing does not disappear from the population but remains present in a population in the undetectable heterozygous state at a constant allele frequency.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na+], 20 mM EDTA, 0.01% Tween-20 and a temperature of 30-50° C., or at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GENECHIP® Mapping Assay Manual, 2004.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), LNAs, as described in Koshkin et al. Tetrahedron 54:3607-3630, 1998, and U.S. Pat. No. 6,268,490, aptamers, and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). In one aspect, an isolated nucleic acid comprises at least about 50, 80 or 90% (on a molar basis) of all macromolecular species present. In a further embodiment, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage analysis" as used herein refers to a method of genetic analysis in which data are collected from affected families, and regions of the genome are identified that co-segregated with the disease in many independent families or over many generations of an extended pedigree. A disease locus may be identified because it lies in a region of the genome that is shared by all affected members of a pedigree.

The term "linkage disequilibrium" or sometimes referred to as "allelic association" as used herein refers to the preferential association of a particular allele or genetic marker with a specific allele, or genetic marker at a nearby chromosomal location more frequently than expected by chance for any particular allele frequency in the population. For example, if locus X has alleles A and B, which occur equally frequently, and linked locus Y has alleles C and D, which occur equally frequently, one would expect the combination AC to occur with a frequency of 0.25. If AC occurs more frequently, then alleles A and C are in linkage disequilibrium. Linkage disequilibrium may result from natural selection of certain combination of alleles or because an allele has been introduced into a population too recently to have reached equilibrium with linked alleles. The genetic interval around a disease locus may be narrowed by detecting disequilibrium between nearby markers and the disease locus. For additional information on linkage disequilibrium see Ardlie et al., Nat. Rev. Gen. 3:299-309, 2002.

The term "lod score" or "LOD" is the log of the odds ratio of the probability of the data occurring under the specific hypothesis relative to the null hypothesis. LOD=log [probability assuming linkage/probability assuming no linkage].

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "monomer/building block" as used herein refers to a member of the set of smaller molecules which can be joined together to form a larger molecule or polymer. The set of monomers includes but is not restricted to, for example, the set of common L-amino acids, the set of D-amino acids, the set of natural or synthetic amino acids, the set of nucleotides (both ribonucleotides and deoxyribonucleotides, natural and unnatural) and the set of pentoses and hexoses. As used herein, monomer refers to any member of a basis set for synthesis of a larger molecule. A selected set of monomers forms a basis set of monomers. For example, the basis set of nucleotides includes A, T (or U), G and C. In another example, dimers of the 20 naturally occurring L-amino acids form a basis set of 400 monomers for synthesis of polypeptides. Different basis sets of monomers may be used in any of the successive steps in the synthesis of a polymer. Furthermore, each of the sets may include protected members which are modified after synthesis.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases. In one aspect "nucleic acids" include cytosine, thymine, and uracil, and adenine and guanine, respectively. See Albert L. Lehninger, Principles of Biochemistry, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, at least 8, and at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized or free-in-solution molecule that can be recognized by a particular target. U.S. Pat. No. 6,582,908 provides an example of arrays having all possible combinations of nucleic acid-based probes having a length of 10 bases, and 12 bases or more. In one embodiment, a probe may consist of an open circle molecule, comprising a nucleic acid having left and right arms whose sequences are complementary to the target, and separated by a linker region. Open circle probes are described in, for instance, U.S. Pat. No. 6,858,412, and Hardenbol et al., Nat. Biotechnol., 21(6):673 (2003). In another embodiment, a probe, such as a nucleic acid, may be attached to a microparticle carrying a distinguishable code. Examples of encoded microparticles, methods of making the same, methods for fabricating the microparticles, methods and systems for detecting microparticles, and the methods and systems for using microparticles are described in U.S. Patent Application Publication Nos. 20080038559, 20070148599, and PCT Application No. WO 2007/081410. Each of which is hereby incorporated by reference in its entirety for all purposes. Examples of nucleic acid probe sequences that may be investigated by this invention include, but are not restricted to, those that are complementary to genes encoding agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "protecting group" as used herein refers to a material which is chemically bound to a reactive functional group on a monomer unit or polymer and which protective group may be removed upon selective exposure to an activator such as a chemical activator, or another activator, such as electromagnetic radiation or light, especially ultraviolet and visible light. Protecting groups that are removable upon exposure to electromagnetic radiation, and in particular light, are termed "photolabile protecting groups."

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, trenches, grooves, raised regions, pins, etched trenches, or the like. Solid supports used in the present invention include any of a variety of fixed organizational support matrices. According to other embodiments, the solid support(s) will take the form of slides, solid chips, beads, resins, gels, microspheres, or other geometric configurations. (See, U.S. Pat. No. 5,744,305, for exemplary substrates). Additionally, the solid supports may be, for example, biological, nonbiological, organic, inorganic, or a combination thereof, and may be in forms including particles, strands, gels, sheets, tubing, spheres, containers, capillaries, pads, slices, films, plates, and slides depending upon the intended use.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as antiprobes. As the term targets is used herein, no difference in meaning is intended. A "Probe Target Pair" is formed when two macromolecules have combined through molecular recognition to form a complex.

The term "wafer" as used herein refers to a substrate having surface to which a plurality of polymers such as oligonucleotide, ribonucleotides, deoxyribonucleotides, peptides, peptide nucleic acids (PNAs), that comprise purine and pyrimidine bases, or other natural, chemically or biochemically modified, non-natural, or derivatized nucleotide bases, that can be bound and thereafter may be diced.

B. Embodiments of the Present Invention

Embodiments of an imaging system and methods of detection are described herein in which data is acquired by scanning probe arrays comprising probe features. In particular, embodiments are described that comprise a CCD based optical architecture using a combination of LED light sources to perform the functions of automatic focus and excitation of fluorescent molecules. Details are described in U.S. patent application Ser. No. 11/379,641 filed on Apr. 21, 2006, which is hereby incorporated by reference herein in its entirety for all purposes.

Figure 2:
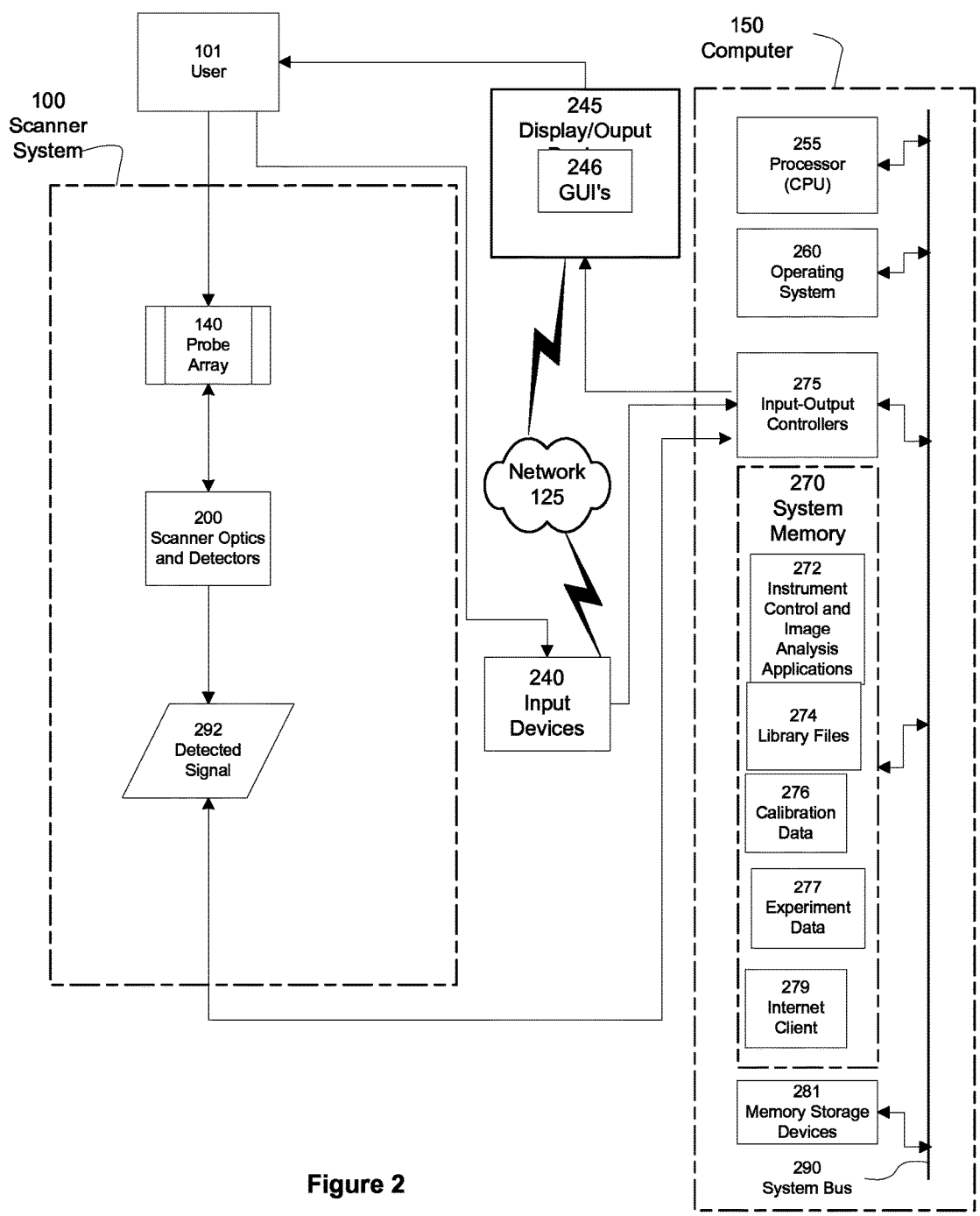
FIG. 2 illustrates a functional block diagram of one embodiment of the scanner-computer system of FIG. 1, including scanner optics and detectors.
Figure 3:
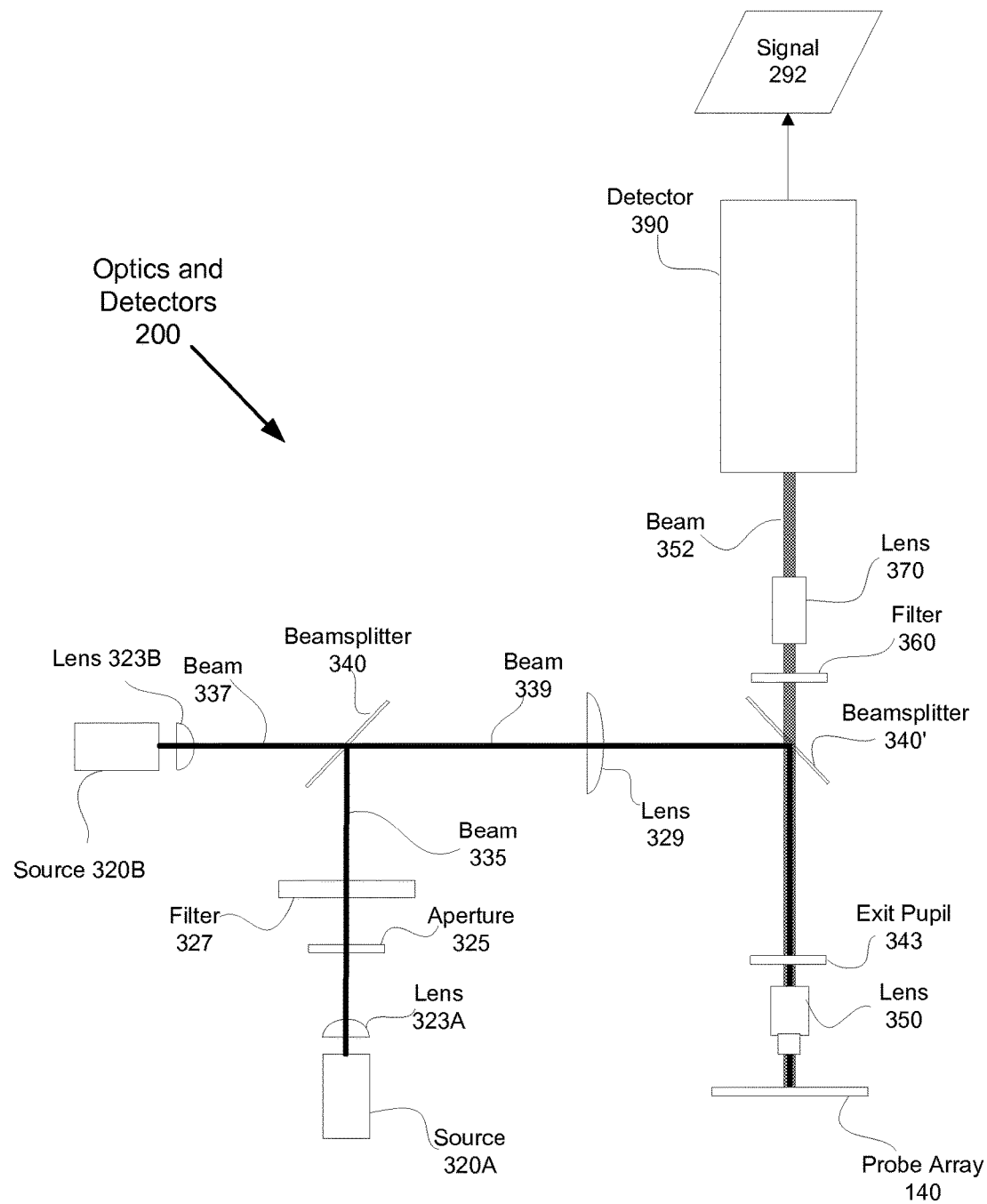
FIG. 3 illustrates a simplified graphical representation of the scanner optics and detectors of FIG. 2, suitable for providing excitation light and the detection of emission signals.

Probe Array 140:

An illustrative example of probe array 140 is provided in FIGS. 1, 2, and 3. Descriptions of probe arrays are provided above with respect to "Nucleic Acid Probe arrays" and other related disclosure. In various implementations, probe array 140 may be disposed in a cartridge or housing such as, for example, the GENECHIP® probe array available from Affymetrix, Inc. of Santa Clara Calif. Examples of probe arrays and associated cartridges or housings may be found in U.S. Pat. Nos. 5,945,334, 6,287,850, 6,399,365, 6,551,817, each of which is also hereby incorporated by reference herein in its entirety for all purposes. In addition, some embodiments of probe array 140 may be associated with pegs or posts, where for instance probe array 140 may be affixed via gluing, welding, or other means known in the related art to the peg or post that may be operatively coupled to a tray, strip or other type of similar substrate. Examples with embodiments of probe array 140 associated with pegs or posts may be found in U.S. patent application Ser. No. 10/826,577, titled "Immersion Array Plates for Interchangeable Microtiter Well Plates", filed Apr. 16, 2004, which is hereby incorporated by reference herein in its entirety for all purposes.

Server 120:

FIG. 1 shows a typical configuration of a server computer connected to a workstation computer via a network. In some implementations any function ascribed to Server 120 may be carried out by one or more other computers, and/or the functions may be performed in parallel by a group of computers.

Typically, server 120 is a network-server class of computer designed for servicing a number of workstations or other computer platforms over a network. However, server 120 may be any of a variety of types of general-purpose computers such as a personal computer, workstation, main frame computer, or other computer platform now or later developed. Server 120 typically includes known components such as a processor, an operating system, a system memory, memory storage devices, and input-output controllers. It will be understood by those skilled in the relevant art that there are many possible configurations of the components of server 120 that may typically include cache memory, a data backup unit, and many other devices. Similarly, many hardware and associated software or firmware components may be implemented in a network server. For example, components to implement one or more firewalls to protect data and applications, uninterruptible power supplies, LAN switches, web-server routing software, and many other components. Those of ordinary skill in the art will readily appreciate how these and other conventional components may be implemented.

Server 120 may employ one or more processing elements that may, for instance, include multiple processors; e.g., multiple Intel® Xeon™ 3.2 GHz processors. As further examples, the processing elements may include one or more of a variety of other commercially available processors such as Itanium® 2 64-bit processors or Pentium® processors from Intel, SPARC® processors made by Sun Microsystems, Opteron™ processors from Advanced Micro Devices, or other processors that are or will become available. Some embodiments of processing elements may also include what are referred to as Multi-core processors and/or be enabled to employ parallel processing technology in a single or multi-core configuration. In addition, those of ordinary skill in the related will appreciate that processing elements may be configured in what is generally referred to as a 32 or 64 bit architecture, or other architectural configurations now known or that may be developed in the future.

The processing elements execute the operating system, which may be, for example, a Windows®-type operating system (such as Windows® XP Professional (which may include a version of Internet Information Server (IIS))) from the Microsoft Corporation; the Mac OS X Server operating system from Apple Computer Corp.; the Solaris operating system from Sun Microsystems, the Tru64 Unix from Compaq, other Unix® or Linux-type operating systems available from many vendors or open sources; another or a future operating system; or some combination thereof. The operating system interfaces with firmware and hardware in a well-known manner, and facilitates the processor in coordinating and executing the functions of various computer programs that may be written in a variety of programming languages. The operating system, typically in cooperation with the processor, coordinates and executes functions of the other components of server 120. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, or other memory storage device. The memory storage device may be any of a variety of known or future devices, including a compact disk drive, a tape drive, a removable hard disk drive, USB or flash drive, or a diskette drive. Such types of memory storage device typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in the system memory and/or the program storage device used in conjunction with the memory storage device.

In some embodiments, a computer program product is described comprising a computer usable medium having control logic (computer software program, including program code) stored therein. The control logic, when executed by the processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

The input-output controllers could include any of a variety of known devices for accepting and processing information from a user, whether a human or a machine, whether local or remote. Such devices include, for example, modem cards, network interface cards, sound cards, or other types of controllers for any of a variety of known input or output devices. In the illustrated embodiment, the functional elements of server 120 communicate with each other via a system bus. Some of these communications may be accomplished in alternative embodiments using network or other types of remote communications.

As will be evident to those skilled in the relevant art, a server application if implemented in software, may be loaded into the system memory and/or the memory storage device through one of the input devices. All or portions of these loaded elements may also reside in a read-only memory or similar device of the memory storage device, such devices not requiring that the elements first be loaded through the input devices. It will be understood by those skilled in the relevant art that any of the loaded elements, or portions of them, may be loaded by the processor in a known manner into the system memory, or cache memory (not shown), or both, as advantageous for execution.

Scanner System 100:

Labeled targets hybridized to probe arrays may be detected using various devices, sometimes referred to as scanners, as described above with respect to methods and apparatus for signal detection. An illustrative device is shown in FIG. 1 as scanner 100, that may incorporate a variety of optical elements such as the example illustrated in FIG. 3 that includes a plurality of optical elements associated with scanner optics and detectors 200. For example, scanners image the targets by detecting fluorescent or other emissions from labels associated with target molecules, or by detecting transmitted, reflected, or scattered radiation. A typical scheme employs optical and other elements to provide excitation light and to selectively collect the emissions.

For example, scanner 100 provides a signal representing the intensities (and possibly other characteristics, such as color that may be associated with a detected wavelength) of the detected emissions or reflected wavelengths of light, as well as the locations on the substrate where the emissions or reflected wavelengths were detected. Typically, the signal includes intensity information corresponding to elemental sub-areas of the scanned substrate. The term "elemental" in this context means that the intensities, and/or other characteristics, of the emissions or reflected wavelengths from this area each are represented by a single value. When displayed as an image for viewing or processing, elemental picture elements, or pixels, often represent this information. Thus, in the present example, a pixel may have a single value representing the intensity of the elemental sub-area of the substrate from which the emissions or reflected wavelengths were scanned. The pixel may also have another value representing another characteristic, such as color, positive or negative image, or other type of image representation. The size of a pixel may vary in different embodiments and could include a 2.5 microns, 1.5 microns, 1.0 micron, or sub-micron pixel size. Two examples where the signal may be incorporated into data are data files in the form *.dat or *.tif as generated respectively by AFFYMETRIX® Microarray Suite (described in U.S. patent application Ser. No. 10/219,882, which is hereby incorporated by reference herein in its entirety for all purposes) or Affymetrix GENECHIP® Operating Software (described in U.S. patent application Ser. No. 10/764,663, which is hereby incorporated by reference herein in its entirety for all purposes) or AFFYMETRIX® command-control Software (described in U.S. patent application Ser. No. 11/279,068, which is hereby incorporated by reference herein in its entirety for all purposes) based on images scanned from GENECHIP® arrays, and AFFYMETRIX® Jaguar™ software (described in U.S. patent application Ser. No. 09/682,071, which is hereby incorporated by reference herein in its entirety for all purposes) based on images scanned from spotted arrays. Examples of scanner systems that may be implemented with embodiments of the present invention include U.S. patent application Ser. Nos. 10/389,194; 10/913,102, both of which are incorporated by reference above; and U.S. patent application Ser. No. 10/846,261, titled "System, Method, and Product for Providing A Wavelength-Tunable Excitation Beam", filed May 13, 2004; and U.S. patent application Ser. No. 11/260,617, titled "System, Method and Product for Multiple Wavelength Detection Using Single Source Excitation", filed Oct. 27, 2005, each of which is hereby incorporated by reference herein in its entirety for all purposes.

Embodiments of the scanner 100 may employ a CCD (Charge Coupled Device) architecture using a CCD or cooled CCD cameras with a wide field of view. For example, a CCD based optical architecture for acquiring images from probe array 140 is described in greater detail below with respect to scanner optics and detectors 200.

Computer 150:

An illustrative example of computer 150 is provided in FIG. 1 and also in greater detail in FIG. 2. Computer 150 may be any type of computer platform such as a workstation, a personal computer, a server, or any other present or future computer. Computer 150 typically includes known components such as a processor 255, an operating system 260, system memory 270, memory storage devices 281, and input-output controllers 275, input devices 240, and display/output devices 245. Display/Output Devices 245 may include display devices that provides visual information, this information typically may be logically and/or physically organized as an array of pixels. A Graphical user interface (GUI) controller may also be included that may comprise any of a variety of known or future software programs for providing graphical input and output interfaces such as for instance GUI's 246. For example, GUI's 246 may provide one or more graphical representations to a user, such as user 101, and also be enabled to process user inputs via GUI's 246 using means of selection or input known to those of ordinary skill in the related art.

It will be understood by those of ordinary skill in the relevant art that there are many possible configurations of the components of computer 150 and that some components that may typically be included in computer 150 are not shown, such as cache memory, a data backup unit, and many other devices. Processor 255 may be a commercially available processor such as an Itanium® or Pentium® processor made by Intel Corporation, a SPARC® processor made by Sun Microsystems, an Athalon™ or Opteron™ processor made by AMD corporation, or it may be one of other processors that are or will become available. Some embodiments of processor 255 may also include what are referred to as Multi-core processors and/or be enabled to employ parallel processing technology in a single or multi-core configuration. For example, a multi-core architecture typically comprises two or more processor "execution cores". In the present example each execution core may perform as an independent processor that enables parallel execution of multiple threads. In addition, those of ordinary skill in the related will appreciate that processor 255 may be configured in what is generally referred to as 32 or 64 bit architectures, or other architectural configurations now known or that may be developed in the future.

Processor 255 executes operating system 260, which may be, for example, a Windows®-type operating system (such as Windows® XP) from the Microsoft Corporation; the Mac OS X operating system from Apple Computer Corp. (such as 7.5 Mac OS X v10.4 "Tiger" or 7.6 Mac OS X v10.5 "Leopard" operating systems); a Unix® or Linux-type operating system available from many vendors or what is referred to as an open source; another or a future operating system; or some combination thereof. Operating system 260 interfaces with firmware and hardware in a well-known manner, and facilitates processor 255 in coordinating and executing the functions of various computer programs that may be written in a variety of programming languages. Operating system 260, typically in cooperation with processor 255, coordinates and executes functions of the other components of computer 150. Operating system 260 also provides scheduling, input-output control, file and data management, memory management, and communication control and related services, all in accordance with known techniques.

System memory 270 may be any of a variety of known or future memory storage devices. Examples include any commonly available random access memory (RAM), magnetic medium such as a resident hard disk or tape, an optical medium such as a read and write compact disc, or other memory storage device. Memory storage devices 281 may be any of a variety of known or future devices, including a compact disk drive, a tape drive, a removable hard disk drive, USB or flash drive, or a diskette drive. Such types of memory storage devices 281 typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 270 and/or the program storage device used in conjunction with memory storage device 281.

In some embodiments, a computer program product is described comprising a computer usable medium having control logic (computer software program, including program code) stored therein. The control logic, when executed by processor 255, causes processor 255 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 275 could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers of input-output controllers 275 could include controllers for any of a variety of known display devices for presenting information to a user, whether a human or a machine, whether local or remote. In the illustrated embodiment, the functional elements of computer 150 communicate with each other via system bus 290. Some of these communications may be accomplished in alternative embodiments using network or other types of remote communications.

As will be evident to those skilled in the relevant art, instrument control and image processing applications 272, if implemented in software, may be loaded into and executed from system memory 270 and/or memory storage device 281. All or portions of applications 272 may also reside in a read-only memory or similar device of memory storage device 281, such devices not requiring that applications 272 first be loaded through input-output controllers 275. It will be understood by those skilled in the relevant art that applications 272, or portions of it, may be loaded by processor 255 in a known manner into system memory 270, or cache memory (not shown), or both, as advantageous for execution. Also illustrated in FIG. 2 are library files 274, calibration data 276, and experiment data 277, and internet client 279 stored in system memory 270. For example, experiment data 277 could include data related to one or more experiments or assays such as excitation wavelength ranges, emission wavelength ranges, extinction coefficients and/or associated excitation power level values, or other values associated with one or more fluorescent labels. Additionally, internet client 279 may include an application enabled to accesses a remote service on another computer using a network that may for instance comprise what are generally referred to as "Web Browsers". In the present example some commonly employed web browsers include Netscape® 8.0 available from Netscape Communications Corp., Microsoft® Internet Explorer 6 with SP 1 available from Microsoft Corporation, Mozilla Firefox® 1.5 from the Mozilla Corporation, Safari 2.0 from Apple Computer Corp., or other type of web browser currently known in the art or to be developed in the future. Also, in the same or other embodiments internet client 279 may include, or could be an element of, specialized software applications enabled to access remote information via a network such as network 125 such as, for instance, the GENECHIP® Data Analysis Software (GDAS) package or Chromosome Copy Number Tool (CNAT) both available from Affymetrix, Inc. of Santa Clara Calif. that are each enabled to access information from remote sources, and in particular probe array annotation information from the NetAffx™ web site hosted on one or more servers provided by Affymetrix, Inc.

Network 125 may include one or more of the many various types of networks well known to those of ordinary skill in the art. For example, network 125 may include a local or wide area network that employs what is commonly referred to as a TCP/IP protocol suite to communicate, that may include a network comprising a worldwide system of interconnected computer networks that is commonly referred to as the internet, or could also include various intranet architectures. Those of ordinary skill in the related arts will also appreciate that some users in networked environments may employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Instrument control and image processing applications 272: Instrument control and image processing applications 272 may comprise any of a variety of known or future image processing applications. Some examples of known instrument control and image processing applications include the AFFYMETRIX® Microarray Suite, and Affymetrix GENECHIP® Operating Software (hereafter referred to as GCOS) applications. Typically, embodiments of applications 272 may be loaded into system memory 270 and/or memory storage device 281 through one of input devices 240.

Some embodiments of applications 272 include executable code being stored in system memory 270. For example, the described embodiments of applications 272 may, for example, include the AFFYMETRIX® Command-Console™ software. Embodiments of applications 272 may advantageously provide what is referred to as a modular interface for one or more computers or workstations and one or more servers, as well as one or more instruments. The term "modular" as used herein generally refers to elements that may be integrated to and interact with a core element in order to provide a flexible, updateable, and customizable platform. For example, as will be described in greater detail below applications 272 may comprise a "core" software element enabled to communicate and perform primary functions necessary for any instrument control and image processing application. Such primary functionality may include communication over various network architectures, or data processing functions such as processing raw intensity data into a .dat file. In the present example, modular software elements, such as for instance what may be referred to as a plug-in module, may be interfaced with the core software element to perform more specific or secondary functions, such as for instance functions that are specific to particular instruments. In particular, the specific or secondary functions may include functions customizable for particular applications desired by user 101. Further, integrated modules and the core software element are considered to be a single software application, and referred to as applications 272.

In the presently described implementation, applications 272 may communicate with, and receive instruction or information from, or control one or more elements or processes of one or more servers, one or more workstations, and one or more instruments. Also, embodiments of server 120 or computer 150 with an implementation of applications 272 stored thereon could be located locally or remotely and communicate with one or more additional servers and/or one or more other computers/workstations or instruments.

In some embodiments, applications 272 may be capable of data encryption/decryption functionality. For example, it may be desirable to encrypt data, files, information associated with GUI's 246, or other information that may be transferred over network 125 to one or more remote computers or servers for data security and confidentiality purposes. For example, some embodiments of probe array 140 may be employed for diagnostic purposes where the data may be associated with a patient and/or a diagnosis of a disease or medical condition. It is desirable in many applications to protect the data using encryption for confidentiality of patient information. In addition, one-way encryption technologies may be employed in situations where access should be limited to only selected parties such as a patient and their physician. In the present example, only the selected parties have the key to decrypt or associate the data with the patient. In some applications, the one-way encrypted data may be stored in one or more public databases or repositories where even the curator of the database or repository would be unable to associate the data with the user or otherwise decrypt the information. The described encryption functionality may also have utility in clinical trial applications where it may be desirable to isolate one or more data elements from each other for the purpose of confidentiality and/or removal of experimental biases.

Various embodiments of applications 272 may provide one or more interactive graphical user interfaces that allows user 101 to make selections based upon information presented in an embodiment of GUI 246. Those of ordinary skill will recognize that embodiments of GUI 246 may be coded in various language formats such as an HTML, XHTML, XML, javascript, Jscript, or other language known to those of ordinary skill in the art used for the creation or enhancement of "Web Pages" viewable and compatible with internet client 279. For example, internet client 379 may include various internet browsers such as Microsoft Internet Explorer, Netscape Navigator, Mozilla Firefox, Apple Safari, or other browsers known in the art. Applications of GUI's 246 viewable via one or more browsers may allow user 101 complete remote access to data, management, and registration functions without any other specialized software elements. Applications 272 may provide one or more implementations of interactive GUI's 246 that allow user 101 to select from a variety of options including data selection, experiment parameters, calibration values, and probe array information within the access to data, management, and registration functions.

In some embodiments, applications 272 may be capable of running on operating systems in a non-English format, where applications 272 can accept input from user 101 in various non-English language formats such as Chinese, French, Spanish etc., and output information to user 101 in the same or other desired language output. For example, applications 272 may present information to user 101 in various implementations of GUI 246 in a language output desired by user 101, and similarly receive input from user 101 in the desired language. In the present example, applications 272 is internationalized such that it is capable of interpreting the input from user 101 in the desired language where the input is acceptable input with respect to the functions and capabilities of applications 272.

Embodiments of applications 272 also include instrument control features, where the control functions of individual types or specific instruments such as scanner 100, an autoloader, or fluid handling system may be organized as plug-in type modules to applications 272. For example, each plug-in module may be a separate component and may provide definition of the instrument control features to applications 272. As described above, each plug-in module is functionally integrated with applications 272 when stored in system memory 270 and thus reference to applications 272 includes any integrated plug-in modules. In the present example, each instrument may have one or more associated embodiments of plug-in module that for instance may be specific to model of instrument, revision of instrument firmware or scripts, number and/or configuration of instrument embodiment, etc. Further, multiple embodiments of plug-in module for the same instrument such as scanner 100 may be stored in system memory 270 for use by applications 272, where user 101 may select the desired embodiment of module to employ, or alternatively such a selection of module may be defined by data encoded directly in a machine readable identifier or indirectly via the array file, library files, experiments files and so on.

The instrument control features may include the control of one or more elements of one or more instruments that could, for instance, include elements of a hybridization device, fluid handling system, autoloader, and scanner 100. The instrument control features may also be capable of receiving information from the one more instruments that could include experiment or instrument status, process steps, or other relevant information. The instrument control features could, for example, be under the control of or an element of the interface of applications 272. In some embodiments, a user may input desired control commands and/or receive the instrument control information via one of GUI's 246. Additional examples of instrument control via a GUI or other interface is provided in U.S. patent application Ser. No. 10/764,663, titled "System, Method and Computer Software Product for Instrument Control, Data Acquisition, Analysis, Management and Storage", filed Jan. 26, 2004, which is hereby incorporated by reference herein in its entirety for all purposes.

In some embodiments, applications 272 may employ what may referred to as an "array file" that comprises data employed for various processing functions of images by applications 272 as well as other relevant information. Generally it is desirable to consolidate elements of data or metadata related to an embodiment of probe array 140, experiment, user, or some combination thereof, to a single file that is not duplicated (i.e. as embodiments of .dat file may be in certain applications), where duplication may sometimes be a source of error. The term "metadata" as used herein generally refers to data about data. It may also be desirable in some embodiments to restrict or prohibit the ability to overwrite data in the array file. New information may be appended to the array file rather than deleting or overwriting information, providing the benefit of traceability and data integrity (i.e. as may be required by some regulatory agencies). For example, an array file may be associated with one or more implementations of an embodiment of probe array 140, where the array file acts to unify data across a set of probe arrays 140. The array file may be created by applications 272 via a registration process, where user 101 inputs data into applications 272 via one or more of GUI's 246. In the present example, the array file may be associated by user 101 with a custom identifier that could include a machine readable identifier such as the machine readable identifiers described in greater detail below. Alternatively, applications 272 may create an array file and automatically associate the array file with a machine readable identifier that identifies an embodiment of probe array 140 (i.e. relationship between the machine readable identifier and probe array 140 may be assigned by a manufacturer). Applications 272 may employ various data elements for the creation or update of the array file from one or more library files, such as library files 274 or other library files.

Alternatively, the array file may comprise pointers to one or more additional data files comprising data related to an associated embodiment of probe array 140. For example, the manufacturer of probe array 140 or other user may provide library files 274 or other files that define characteristics such as probe identity; dimension and positional location (i.e. with respect to some fiducial reference or coordinate system) of the active area of probe array 140; various experimental parameters; instrument control parameters; or other types of useful information. In addition, the array file may also contain one or more metadata elements that could include one or more of a unique identifier for the array file, human readable form of a machine readable identifier, or other metadata elements. In addition, applications 272 may store data (i.e. as metadata, or stored data) that includes sample identifiers, array names, user parameters, event logs that may for instance include a value identifying the number of times an array has been scanned, relationship histories such as for instance the relationship between each .cel file and the one or more .dat files that were employed to generate the .cel file, and other types of data useful in for processing and data management.

For example, user 101 and/or automated data input devices or programs (not shown) may provide data related to the design or conduct of experiments. User 101 may specify an Affymetrix catalogue or custom chip type (e.g., Human Genome U133 plus 2.0 chip) either by selecting from a predetermined list presented in one or more of GUI's 246 or by scanning a bar code, Radio Frequency Identification (RFID), magnetic strip, or other means of electronic identification related to a chip to read its type, part no., array identifier, etc. Applications 272 may associate the chip type, part numbers, array identifier with various scanning parameters stored in data tables or library files, such as library files 274 of computer 150, including the area of the chip that is to be scanned, the location of chrome elements or other features on the chip used for auto-focusing, the wavelength or intensity/power of excitation light to be used in reading the chip, and so on. Also, some embodiments of applications 272 may encode array files in a binary type format that may minimize the possibility of data corruption. However, applications 272 may be further enabled to export an array file in a number of different formats.

Also, in the same or alternative embodiments, applications 272 may generate or access what may be referred to as a "plate" file. The plate file may encode one or more data elements such as pointers to one or more array files, and may include pointers to a plurality of array files.

In some embodiments, raw image data is acquired from scanner 100 and operated upon by applications 272 to generate intermediate results. For example, raw intensity data, represented as detected signal 292 of FIG. 2, acquired from scanner 100 may be directed to a .dat file generator and written to data files (*.dat) that comprises an intensity value for each pixel of data acquired from a scan of an embodiment of probe array 140. In the same or alternative embodiments it may be advantageous to scan sub areas (that may be referred to as sub arrays or sections of the array) of probe array 140 where detected signal 292 for each sub area scanned may be written to an individual embodiment of a .dat file. Continuing with the present example, applications 272 may also encode a unique identifier for each .dat file as well as a pointer to an associated embodiment of an array file as metadata into each .dat file generated. The term "pointer" as used herein generally refers to a programming language datatype, variable, or data object that references another data object, datatype, variable, etc. using a memory address or identifier of the referenced element in a memory storage device such as in system memory 270. In some embodiments the pointers comprise the unique identifiers of the files that are the subject of the pointing, such as for instance the pointer in a .dat file comprises the unique identifier of the array file. Additional examples of the generation and image processing of sub arrays is described in U.S. patent application Ser. No. 11/289,975, titled "System, Method, and Product for Analyzing Images Comprising Small Feature Sizes", filed Nov. 30, 2005, which is hereby incorporated by reference herein in its entirety for all purpose.

Also, applications 272 may also include a .cel file generator that may produce one or more .cel files (*.cel) by processing each .dat file. Alternatively, some embodiments of .cel file generator may produce a single .cel file from processing multiple .dat files such as with the example of processing multiple sub-arrays described above. Similar to the .dat file described above each embodiment of .cel file 425 may also include one or more metadata elements. For example, applications 272 may encode a unique identifier for each .cel file as well as a pointer to an associated array file and/or the one or more .dat files used to produce the .cel file.

Each .cel file contains, for each probe feature scanned by scanner 100, a single value representative of the intensities of pixels measured by scanner 100 for that probe. For example, this value may include a measure of the abundance of tagged mRNA's present in the target that hybridized to the corresponding probe. Many such mRNA's may be present in each probe, as a probe on a GENECHIP® probe array may include, for example, millions of oligonucleotides designed to detect the mRNA's. Alternatively, the value may include a measure related to the sequence composition of DNA or other nucleic acid detected by the probes of a GENECHIP® probe array. As described above, applications 272 receives image data derived from probe array 140 using scanner 100 and generates a .dat file that is then processed by applications 272 to produce a .cel intensity file, where applications 272 may utilize information from an array file in the image processing function. For instance, the .cel file generator may perform what is referred to as grid placement methods on the image data in each .dat file using data elements such as dimension information to determine and define the positional location of probe features in the image. Typically, the .cel file generator associates what may be referred to as a grid with the image data in a .dat file for the purpose of determining the positional relationship of probe features in the image with the known positions and identities of the probe features. The accurate registration of the grid with the image is important for the accuracy of the information in the resulting .cel file. Also, some embodiments of .cel file generator may provide user 101 with a graphical representation of a grid aligned to image data from a selected .dat file in an implementation of GUI 246, and further enable user 101 to manually refine the position of the grid placement using methods commonly employed such as placing a cursor over the grid, selecting such as by holding down a button on a mouse, and dragging the grid to a positional relationship with the image. Applications 272 may then perform methods sometimes referred to as "feature extraction" to assign a value of intensity for each probe represented in the image as an area defined by the boundary lines of the grid. Examples of grid registration, methods of positional refinement, and feature extraction are described in U.S. Pat. Nos. 6,090,555, 6,611,767, 6,829,376, and U.S. patent application Ser. Nos. 10/391,882, and 10/197,369, each of which is hereby incorporated by reference herein in their entirety for all purposes.

As noted, another file that may be generated by applications 272 is .chp file 435 using a .chp file generator. For example, each .chp file is derived from analysis of a .cel file combined in some cases with information derived from an array file, other lab data and/or library files 274 that specify details regarding the sequences and locations of probes and controls. In some embodiments, a machine readable identifier associated with probe array 140 may indicate the library file directly or indirectly via one or more identifiers in the array file, to employ for identification of the probes and their positional locations. The resulting data stored in the .chp file includes degrees of hybridization, absolute and/or differential (over two or more experiments) expression, genotype comparisons, detection of polymorphisms and mutations, and other analytical results.

In some alternative embodiments, user 101 may employ different applications to process data such as an independent analysis application. Embodiments of an analysis application may comprise any of a variety of known or probe array analysis applications, and particularly analysis applications specialized for use with embodiments of probe array 140 designed for genotyping or expression applications. Various embodiments of analysis application may exist such as applications developed by the probe array manufacturer for specialized embodiments of probe array 140, commercial third party software applications, open source applications, or other applications known in the art for specific analysis of data from probe arrays 140. Some examples of known genotyping analysis applications include the Affymetrix GENECHIP® Data Analysis System (GDAS), Affymetrix GENECHIP® Genotyping Analysis Software (GTYPE), Affymetrix GENECHIP® Targeted Genotyping Analysis Software (GTGS), and Affymetrix GENECHIP® Sequence Analysis Software (GSEQ) applications. Additional examples of genotyping analysis applications may be found in U.S. application Ser. Nos. 10/657,481, 10/986,963, and 11/157,768, each of which is hereby incorporated by reference herein in their entirety for all purposes. Typically, embodiments of analysis applications may be loaded into system memory 270 and/or memory storage device 281 through one of input devices 240.

Some embodiments of analysis applications include executable code being stored in system memory 270. Applications 272 may be enabled to export .cel files, .dat files, or other files to an analysis application or enable access to such files on computer 150 by the analysis application. Import and/or export functionality for compatibility with specific systems or applications may be enabled by one or more integrated modules as described above with respect to plug-in modules. For example, an analysis application may be capable of performing specialized analysis of processed intensity data, such as the data in a .cel file. In the present example, user 101 may desire to process data associated with a plurality of implementations of probe array 140 and therefore the analysis application would receive a .cel file associated with each probe array for processing. In the present example, applications 272 forwards the appropriate files in response to queries or requests from the analysis application.

In the same or alternative examples, user 101 and/or the third party developers may employ what are referred to as software development kits that enable programmatic access into file formats, or the structure of applications 272. Therefore, developers of other software applications such as the described analysis application may integrate with and seamlessly add functionally to or utilize data from applications 272 that provides user 101 with a wide range of application and processing capability. Additional examples of software development kits associated with software or data related to probe arrays are described in U.S. Pat. No. 6,954,699, and U.S. patent application Ser. Nos. 10/764,663 and 11/215,900, each of which is hereby incorporated by reference herein in its entirety for all purposes.

Additional examples of .cel and .chp files are described with respect to the Affymetrix GENECHIP® Operating Software or AFFYMETRIX® Microarray Suite (as described, for example, in U.S. patent application Ser. Nos. 10/219,882 and 10/764,663, both of which are hereby incorporated herein by reference in their entireties for all purposes). For convenience, the term "file" often is used herein to refer to data generated or used by applications 272 and executable counterparts of other applications such as analysis application 380, where the data is written according a format such as the described .dat, .cel, and .chp formats. Further, the data files may also be used as input for applications 272 or other software capable of reading the format of the file.

Those of ordinary skill in the related art will appreciate that one or more operations of applications 272 may be performed by software or firmware associated with various instruments. For example, scanner 100 could include a computer that may include a firmware component that performs or controls one or more operations associated with scanner 100.

Yet another example of instrument control and image analysis applications is described in U.S. patent application Ser. No. 11/279,068, titled "System, Method and Computer Product for Simplified Instrument Control and File Management", filed Apr. 7, 2006, which is hereby incorporated by reference herein in its entirety for all purposes.

Scanner Optics and Detectors 200:

FIG. 3 provides a simplified graphical example of possible embodiments of optical elements associated with scanner 100, illustrated as scanner optics and detectors 200.

One embodiment of scanner optics and detectors 200 is shown in FIG. 3. Source 320A may be, for example, a "Luxeon III" light-emitting diode manufactured by Lumileds Lighting LLC (San Jose Calif., model LXHL-LE3C or LXHL-LM3C) and having a nominal central wavelength of 505 nm or 530 nm. The list price of this LED is fairly inexpensive. Similar LEDs may be available from other manufacturers such as Cree Inc (Durham N.C.). The actual central wavelength can differ from the nominal central wavelength by up to 15 nm, and the emission spectrum of the LED has a full width at half maximum of approximately 30 nm. Source 320A emits light over approximately 2-pi steradians (one hemisphere). A portion of the light emitted by source 320A is collimated by lens 323A, which may by an aspheric lens, for example, having a focal length of 17 mm and a diameter of 25 mm (Newport Corp, Irvine Calif., model KPA031-C).

Source 320B maybe, for example, a "Luxeon" light-emitting diode having a nominal central wavelength of 590 nm (Lumileds Lighting LLC, model LXHL-ML1D). A portion of the light emitted by source 320B is collimated by lens 323B, which may be also an aspheric lens having a focal length of 17 mm and a diameter of 25 mm.

The purpose of source 320A is to excite fluorescence from labeled target molecules that are hybridized to probe array 140. Source 320B is used for autofocusing, as will be described below. Alternatively, some embodiments of scanner 100 may employ a single embodiment of source 320 capable of performing both the excitation and autofocus functions.

Collimated beam 335 generated by lens 323A passes through aperture 325 and filter 327. Aperture 325 is an 11 mm×8.5 mm rectangular opening in a thin black-anodized aluminum disk. Therefore, immediately after passing through aperture 325, beam 335 has a rectangular cross section. Filter 327 is a bandpass filter that efficiently transmits light at wavelengths of 470-550 nm and absorbs or reflects light at other wavelengths, for example, the filter at Chroma Technology Corp, Rockingham Vt., model HQ510/80. Similar filters are manufactured by Omega Optical Inc (Brattleboro Vt.) and Semrock Inc (Rochester N.Y.). Alternatively, filter 327 may be a 550-nm shortpass filter that efficiently transmits light at wavelengths shorter than 550 nm and blocks longer wavelengths. Although source 320A has a nominal central wavelength of 505 nm or 530 nm, it emits some light at wavelengths up to 600 nm or even longer. The purpose of filter 327 is to prevent this long-wavelength light from reaching probe array 140 and the detector 390.

Beamsplitter 340 reflects beam 335 and transmits beam 337, in effect combining the two beams into a single beam, beam 339. Beamsplitter 340 is a longpass dichroic beamsplitter that efficiently reflects light at 470-550 nm and efficiently transmits light at 570-610 nm. Beamsplitter 340 can be a custom dichroic beamsplitter manufactured by a company such as Chroma Technology Corp or an commercially available color-separation filter, for example, a filter manufactured by a company such as Cheshire Optical (Keene, N.H.). Alternatively, filter 340 can be a spectrally neutral beamsplitter (for example, a reflective neutral-density filter) that reflects a portion of beam 335 and transmits a portion of beam 337. In FIG. 3, beam 335 is orthogonal to beam 337, and beamsplitter 340 operates at an angle of incidence of 45 degrees, but other geometric arrangements are possible.

Beam 339 passes through lens 329, which may be, for example, a piano-convex lens having a focal length of 150 mm (Edmund Industrial Optics, Barrington, N.J., model 32-975), and is reflected by beamsplitter 340', which is a longpass dichroic beamsplitter similar to beamsplitter 340. Lens 329 focuses beam 339 onto exit pupil 343 of lens 350. Beam 339 passes through lens 350, which may be, for example, a Nikon CFI Plan Fluor 10× microscope objective having a focal length of 20 mm and a numerical aperture of 0.3, and reaches probe array 140.

The purpose of the optical train described above is to illuminate probe array 140 efficiently and uniformly.

For convenience, in the following discussion we use the thin-lens approximation to describe all of the lenses. The distance from source 320A to lens 323A is equal to the focal length of lens 323A, and the distance from lens 329 to exit pupil 343 is equal to the focal length of lens 329. Therefore an image of source 320A is formed at exit pupil 343. The size of this image is equal to the size of source 320A multiplied by the focal length of lens 329 and divided by focal length of lens 323A. For maximum illumination efficiency, the focal lengths of lenses 323A and 329 should be chosen so that the image of source 320A approximately fills or slightly over-fills exit pupil 343.

The distance from exit pupil 343 to lens 350 is equal to the focal length of lens 350 if lens 350 is telecentric, as most microscope objectives are. If lens 350 is not telecentric, the distance from exit pupil 343 to lens 350 may be zero.

The distance from aperture 325 to lens 329 is equal to the focal length of lens 329, and the distance from lens 350 to probe array 140 is equal to the focal length of lens 350. Therefore an image of aperture 325 is formed at probe array 140. The size of this image is equal to the size of aperture 325 multiplied by the focal length of lens 350 and divided by the focal length of lens 329. Probe array 140 is uniformly illuminated if aperture 325 is uniformly filled by light from source 320A.

The purpose of aperture 325 is to match the illuminated area of probe array 140 to the field of view of detector 390. The dimensions of aperture 325, and the focal lengths of lenses 350 and 329, should be chosen so that the illuminated area of probe array 140 is equal to or slightly greater than the field of view of the detector 390. Illuminating an unnecessarily large area is undesirable because it increases the amount of stray light reaching the detector 390 and because most fluorescent labels are susceptible to photobleaching. However, aperture 325 can optionally be omitted. In this case, the distance from lens 323A to lens 329 is equal to the focal length of lens 329, and an image of the pupil of lens 323A is formed at probe array 140. Probe array 140 is uniformly illuminated if the pupil of lens 323A is uniformly filled by light from source 320A. This optical arrangement is generally referred to as Kohler illumination.

Similarly, the distance from source 320B to lens 323B is equal to the focal length of lens 323B, and the distance from lens 323B to lens 329 is equal to the focal length of lens 329. An image of source 320B is formed at exit pupil 343, and an image of the pupil of lens 320B is formed at probe array 140.

Labeled target molecules bound to probe array 140 fluoresce when illuminated by light from source 320A. A portion of the fluorescent light emitted by the labeled target molecules is collected and collimated by lens 350. The resulting fluorescent beam 352 is transmitted through beamsplitter 340' and filter 360 and is focused by lens 370 onto the detector 390. Filter 360 may be a 570-610 nm bandpass, for example the filter at Chroma Technology Corp, Rockingham, Vt., model HQ590/40, or a 570-nm longpass filter. The purpose of filter 360 is to transmit as much of the desired fluorescence as possible while blocking undesired light. Undesired light consists primarily of light from source 320A that is reflected or back-scattered by probe array 140 or by the housing or support structure of probe array 140. Undesired light can also consist of fluorescence, phosphorescence, or Raman scattering from glass, glue, plastic, contaminants on the surface of probe array 140, etc; this undesired light can be blocked by filter 360 if it has an emission spectrum that is sufficiently different from the emission spectrum of the fluorophore.

The LED, bandpass filter, and dichroic beamsplitter wavelengths described above are appropriate if the target molecules are labeled with R-phycoerythrin. These wavelengths may need to be altered if other fluorophores are used. Other fluorophores may include, for example, fluorescein, rhodamine, or cyanine dyes; lanthanide-chelate fluorophores; semiconductor nanocrystals available from Quantum Dot Corp (Hayward, Calif.) or Evident Technologies (Troy, N.Y.); and FRET (fluorescence resonant energy transfer) labels.

For efficient fluorescence excitation, source 320A needs to emit light at wavelengths that are strongly absorbed by the fluorophore, and filter 327 needs to have high transmittance at these wavelengths. Filter 360 needs to have high transmittance at the wavelengths at which the fluorophore emits light. The passbands of filter 327 and filter 360 should not overlap.

Light Source and Electronics

In one embodiment, each LED light source is driven in constant-current mode by a Texas Instruments model PT6214 regulator. The PT6214 is primarily intended as a voltage source but can be configured as a current source by means of a current-sensing feedback resistor. Alternatively, a variety of other LED drivers are commercially available. When the current is set to 0.9 A (which is 90 percent of the maximum recommended current for the Luxeon III LED), the heat produced by the LED is approximately 3 W. Each LED is mounted on a finned heat sink and optionally cooled by a small fan. Each LED can be turned on and off by means of a digital (TTL) signal (buffered by an SN7407 or similar open-collector buffer) applied to the "Inhibit" pin of the PT6214. The TTL signals can be supplied by a digital input-output board installed in computer 150, or by auxiliary digital outputs of the motion controller, or by auxiliary digital outputs of the detector 390. LED efficiency decreases as temperature increases. Optionally the LEDs can be thermoelectrically cooled or liquid-cooled, but these methods add to the cost and complexity of the instrument.

Electronically the instrument is very simple. The instrument may be controlled by a standard desktop or laptop computer, or optionally by an embedded computer in the scanner system 100. The computer communicates with the camera and the motion controller by means of, for example, an IEEE-1394 (FireWire) interface and an RS-232 or RS-485 interface respectively. No frame grabbers or other data acquisition boards are required. The only custom circuit board required may be the very simple circuit board used to control the LEDs. Power to the camera is supplied over the IEEE-1394 cable. Power to the motion controller and the LEDs is supplied by a 12 V, 6.5 A switching power supply, for example, the power supply commercially available at Digi-Key Corp, Thief River Falls Minn., model SPN75-12S or similar. Software to control the instrument is written in Microsoft Visual Basic, Visual C++, or another suitable language.

Examples of Detectors and Imaging Optics

In one embodiment, the detector 390 may be a scientific-grade digital camera (for example, Hamamatsu Corp, Bridgewater N.J., model C8484-05G) containing a CCD (charge-coupled device) sensor. The sensor contains a rectangular array of 1.37 million (1344×1024) light-sensitive pixels. Each pixel is 6.45 microns square. The overall size of the light-sensitive area of the sensor is therefore 6.6048 mm×8.6688 mm. Detection quantum efficiency at 590 nm exceeds 60 percent. The camera has 12-bit digital output. The Hamamatusu C8484-05G model is an uncooled camera, and dark current is approximately 1 electron/pixel/second when ambient temperature is near 250 C. Dark current does not contribute significantly to camera noise for integrations as long as 10 seconds. A thermoelectrically cooled version (C8484-03G) is available but more expensive. Other similar cameras are available from other manufacturers such as Photometrics (Tucson, Ariz.), Cooke Corp (Romulus, Mich.), and Sensovation (Belmont, Calif.). Most of these cameras contain a Sony model ICX285AL CCD sensor.

In another embodiment, Lens 370 is constructed from two achromatic cemented doublets (for example, Newport Corp, Irvine, Calif., model PAC067), each having a focal length of 250 mm and a diameter of 25.4 mm. Similar lenses are available from several other suppliers. This combination of lenses has a focal length of 126.28 mm at 590 nm when the air space between the 2 achromats is 1 mm. The focal length is dependent on the air space. For example, the focal length is 129 mm when the air space is 11.42 mm. Optical design software, for example, such as Zemax (Zemax Development Corp, San Diego, Calif.) or Oslo (Lambda Research Corp, Littleton, Mass.) can be used to calculate the optical properties of the lens combination.

In FIG. 3, an image of a probe array 140 is formed at the detector 390. A 6.45 micron pixel size camera, a 20 mm focal length for the 350 lens, and a 129 mm focal length for 370 lens are provided as discussed above according to one embodiment. The effective pixel size at the probe array 140 is equal to the pixel size of the detector 390 multiplied by the focal length of the lens 350 and divided by the focal length of lens 370. Therefore, in this embodiment, the effective pixel size would be 1.00 micron. In addition, since the sensor of the detector contains a rectangular array of 1.37 million (1344×1024) light-sensitive pixels, the field of view of the detector 390 would be 1.344 mm×1.024 mm. The size of the area illuminated by source 320A is the size of the aperture 325, for example, an 11 mm×8.5 mm. In this example, the size of the area illuminated by source 320A (11 mm×8.5 mm) is slightly larger than the field of view of the detector 390 (1.344 mm×1.024 mm). In one embodiment, the focal lengths 370 and 350 may be optimized as discussed below to produce an illuminated area of probe array 140 that is closer in size to the field of view of the detector 390.

Different systems are described below by utilizing four microscope objectives that are described in the table below. In this table, depth of field and Airy disk diameter are shown for a wavelength of 590 nm. "Cover glass thickness" in this table means the cover glass thickness that the objective is designed for (which might not be the cover glass thickness at which it is actually used).

| Manufacturer | Nikon | Nikon |
| --- | --- | --- |
| Model | CFI Plan Apochromat 4x | CFI Plan Fluor 10x |
| Focal length (mm) | 50 | 20 |
| Numerical aperture | 0.2 | 0.3 |
| Field of view (mm, diameter) | 6.25 | 2.5 |
| Exit pupil diameter (mm) | 20 | 12 |
| Depth of focus (microns) | +/−7.38 | +/−3.28 |
| Airy disk diameter (microns) | 3.60 | 2.40 |
| Cover glass thickness (mm) | 0 | 0.17 |

| Manufacturer | Olympus | Nikon |
| --- | --- | --- |
| Model | UPLSAPO 10x | CFI Plan Fluor ELWD 60x C |
| Focal length (mm) | 18 | 3.333 |
| Numerical aperture | 0.4 | 0.7 |
| Field of view (mm, diameter) | 2.65 | 0.416 |
| Exit pupil diameter (mm) | 14.4 | 4.666 |
| Depth of focus (microns) | +/−1.84 | +/−0.60 |
| Airy disk diameter (microns) | 1.80 | 1.03 |
| Cover glass thickness (mm) | 0.17 | 0.5-1.5 |

Optical terms such as "Airy disk diameter," "numerical aperture," etc. are well-known to those of ordinary skill in the art and are described in references such as Modern Optical Engineering (W. J. Smith, McGraw-Hill, 2000) and Optical System Design (R. E. Fischer and B. Tadic-Galeb, McGraw-Hill, 2000).

Airy disk diameter is inversely proportional to numerical aperture; therefore, spatial resolution increases as numerical aperture increases. In addition, fluorescence collection efficiency is proportional to the square of the numerical aperture. For these reasons, a high numerical aperture is desirable. On the other hand, the diameter of the field of view of a microscope objective is inversely proportional to the nominal magnification (4×, 10×, 60×, etc); and as shown in the table, numerical aperture is low when nominal magnification is low. Furthermore, the depth of focus is inversely proportional to the square of the numerical aperture, meaning that tight autofocus tolerances are required if a high numerical aperture objective is used. For these reasons, the choice of microscope objective depends on the application.

In one embodiment, a Nikon CFI Plan Fluor 10× objective and an effective pixel size of 1 micron are provided, as described above. The center-to-center distance between the features on probe array 140 is between approximately 5 and 10 microns.

In another embodiment, an Olympus UPLSAPO 10× objective, an effective pixel size of 1 micron, and a focal length 370 of 116.1 mm are provided. The Olympus objective has a higher numerical aperture than the Nikon CFI Plan Fluor 10×, enabling more fluorescent photons to be collected per unit time.

In an alternate embodiment, a center-to-center distance of 1 micron between features on probe array 140, a Nikon CFI Plan Fluor ELWD 60× C lens 350, and a commercially available achromatic cemented doublet having a focal length of 120 mm lens 370 are provided. This combination of lenses gives an effective pixel size of 0.179 microns (6.45 microns multiplied by 3.333 mm and divided by 120 mm).

As another alternative, lens 350 is a Nikon CFI Plan Apochromat 4×. Lens 370 has a focal length of 117 mm and is made from three commercially available achromats (two with focal lengths of 300 mm and one with a focal length of 400 mm). Effective pixel size is 2.75 microns (6.45 microns multiplied by 50 mm and divided by 117 mm). The field of view of the detector 390 is 2.8 mm×3.7 mm. This configuration can be useful if the center-to-center distance between features on probe array 140 is larger than approximately 14 microns.

Correction of Spherical Aberration

Most standard microscope objectives exhibit minimal spherical aberration when the object being scanned is on a cover glass with a thickness of, for example, 170 microns which is located between the objective and the focal plane. Objectives intended for use with thicker cover glasses exist, but they are not necessarily available with the desired focal length and numerical aperture. Undesired spherical aberrations can be created when the object being scanned is thicker, for example, an Affymetrix array cartridge (See, U.S. Pat. Nos. 5,445,934, 5,744,305, 5,945,334, 6,140,044, 6,261,776, 6,291,183, 6,346,413, 6,399,365, 6,420,169, 6,551,817, 6,610,482, 6,733,977, and 6,955,915 for examples of array cartridges), which is a probe array with a substrate thickness of approximately 700 microns, assembled in a housing. Furthermore, the spherical aberrations can be larger when the probe array 140 is immersed in a scan tray, for example, an Affymetrix array plate (See, for example, U.S. patent application Ser. No. 11/347,654 for examples of array plate and scan plates), which is mounted on a peg that is immersed in a scan tray during scanning. The increased spherical aberration is caused by the thick window at the bottom of the scan tray and the presence of an aqueous liquid layer between the window and the probe array. Spherical aberration has both a magnitude and a sign and therefore, may be corrected in at least 3 ways according to an embodiment of the invention.

The first method comprises using a custom tube lens. In this method, the spherical aberration produced in the custom tube lens may be utilized by cancelling the spherical aberration caused by, for example, the scan tray window and the liquid layer.

The second method comprises using an infinite-conjugate microscope objective at a finite conjugate ratio and is described below. An infinite-conjugate objective at a finite conjugate ratio causes spherical aberration. Therefore, a finite conjugate ratio may be chosen appropriately such that the resulting spherical aberration may cancel the spherical aberration caused by the peg plate window and liquid. The third method comprises using a combination of method 1 and method 2 described above. Further details of these methods are described below.

In one embodiment, a microscope objective is optimized to create an amount of spherical aberration to cancel the spherical aberration created from using a thick cover glass. In an alternative embodiment, a standard microscope object may be used with a lens 370 that can be designed to reduce or eliminate the spherical aberration caused by the thick window. In a further embodiment, the lens 370 is well-corrected for off-axis aberrations such as coma, field curvature, lateral color, astigmatism, and distortion.

The microscope objectives discussed above are infinite-conjugate objectives, meaning that they are designed for use at infinite conjugate ratio. Spherical aberration can result when an infinite-conjugate objective that is designed for a particular cover glass thickness is used with that cover glass thickness but at a finite conjugate ratio. However, the spherical aberration caused by the cover glass can be cancelled by using the objective at a finite conjugate ratio when an infinite-conjugate objective is used with a cover glass thickness that it was not designed for. See S. Stallinga, "Finite conjugate spherical aberration compensation in high numerical-aperture optical disc readout," *Applied Optics* 44, 7307-7312 (2005), and references contained therein. The distance from the second principal point of lens 370 to the CCD sensor in the camera 390 is equal to the focal length of lens 370 when objective 350 is used at infinite conjugate ratio. The distance from the second principal point of lens 370 to the CCD sensor in the camera 390 can be several millimeters less than the focal length of lens 370 when objective 350 is used at a finite conjugate ratio.

In one embodiment, lens 370 includes one or more custom optical elements to correct off-axis aberration. Examples of lenses are shown in the table below. The 370 lens uses two commercially available cemented doublets and one custom cemented doublet according to an embodiment. In a further embodiment, the lens 370 is used with an Olympus UPLSAPO 10× objective.

| Radius of curvature (mm) | Thickness (mm) | Material | Notes |
| --- | --- | --- | --- |
| 205.72 | 4.0 | SF5 | Edmund Optics 32923 |
| 70.73 | 8.5 | BK7 | |
| −98.66 | 1.0 | air | |
| 667.68 | 4.0 | SF5 | Edmund Optics 45270 |
| 224.08 | 6.0 | BK7 | |

-continued

| Radius of curvature (mm) | Thickness (mm) | Material | Notes |
|---|---|---|---|
| −305.31 | 67.0 | air | |
| 16.916 | 6.0 | S-TIL6 | custom lens |
| −40.831 | 3.0 | S-BAM4 | |
| 14.27 | 25.0 | air | image plane |

In one embodiment, the instrument is used to obtain images of a DNA array having a synthesis area of, for example, 5.9 mm×5.9 mm. Because the synthesis area is much larger than the field of view of the detector 390, the array is divided into, for example, 49 sub-arrays, each having dimensions of approximately 850 microns×850 microns. Alternatively, the array is divided into 35 sub-arrays, each having dimensions of approximately 850 microns×1180 microns. Probe array 140 is positioned so that the first sub-array is centered in the field of view of the detector 390, focus is adjusted (as explained below), and an image of the first sub-array is obtained. This image is displayed on the computer screen as a gray-scale or false-color image and written to disk in, for example, Affymetrix "dat" format, "tif" format, or any other desired format. Probe array 140 is then moved so that the second sub-array is centered in the field of view of the detector 390. The focus is adjusted and an image of the second sub-array is obtained. These steps are repeated until all the sub-arrays are imaged. In an alternate embodiment, 2 images of each sub-array are taken: a short exposure (for example, a 0.2-second integration) to capture data from bright features, and a long exposure (for example, a 2-second integration) to improve the signal-to-noise ratio for dim features.

Figure 4A:
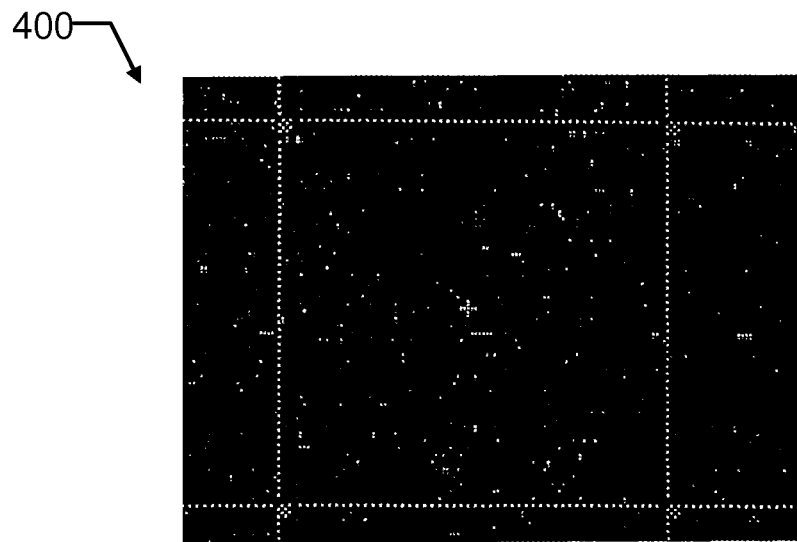
FIGS. 4A and 4B illustrate images of a sub-array.

FIG. 4A shows an example of an image of a sub-array 400, specifically, a fluorescence image of a central sub-array. The nominal size of each feature is 8 microns×8 microns. (The center-to-center feature spacing is 8 microns×8 microns. The actual size of each feature is 6 microns×6 microns. There are 2-micron blank streets between features.)

In one embodiment, an inexpensive translation stage provides sufficient accuracy because each sub-array is about 200 microns smaller than the field of view of the detector 390. Thus, the centration of each sub-array in the field of view can be approximated.

In another embodiment, dark-field and bright-field correction are performed on the images. Dark-field correction is particularly desirable when using an uncooled camera for long integrations. "Hot pixels," which have much higher dark current than the other pixels in the detector, show up as bright spots in the image if dark-field correction is not performed. Bright-field correction is particularly useful if source 320A illuminates the field of view of the detector 390 with non-uniform power density. Both dark-field and bright-field correction are well known to those of ordinary skill in the art.

According to one embodiment, a set up method for imaging a probe array is provided. A surface on the probe array which includes a plurality of fiducials is provided. The fiducials are focused and measured. The measurements describes a relative position of each fiducial. The measurement data are transmitted to a computer that includes a surface fitting algorithm. A surface profile is calculated on the computer that employs the surface fitting algorithm and the transmitted measurement data. One or more surface non-flatness parameters are adjusted based on the calculations. The surface non-flatness parameters are parameters that can be changed to improve the image flatness of the surface. Examples of surface non-flatness parameters include array tilt, stage movement effect and optical parameters, such as the choice of lens. The flatness of the surface can also be improved by adjusting a focal plane, for example, by moving a lens or the camera. The steps described above are repeated until the relative distance of each fiducial on the probe array are positionally optimized for setting up the probe array to be imaged.

In alternate embodiments, the method may include a number of fiducials, for example, at least 4, at least 5 and at least 9 fiducials. The surface fitting algorithm may include a least square, sub-plane surface fit, and B spline surface fit.

In another embodiment, the set up method includes a tilt stage which is described later in the application. The focusing includes tilting the tilt stage so that the array surface is made parallel to a focal plane of a microscope objective.

Translation/Tilt Stage

Depth of focus according to the standard textbook formula used in the field is lambda /NA$^2$, where lambda=wavelength and NA=numerical aperture. There can be significant variations in focus across a sub-array if the depth of focus of lens 350 (for example, see FIG. 3) is short. For example, at 590 nm (the central wavelength of a typical phycoerythrin emission filter), where a probe array 140 is mounted on a peg that is immersed in a 4-peg or 96-peg scan tray, the depth of focus of lens 350 can be less than 4 microns. To improve the focus across a sub-array, a probe array 140 can be mounted on a 2-axis tilt stage such that the pitch, yaw and roll can be adjusted during the autofocus process. During the autofocus process, the tilt stage can be tilted so that the peg surface is made parallel to the focal plane of the microscope objective according to an embodiment of the present invention. If the peg surface is tilted with respect to the focal plane of the microscope objective and a perfect focus in the middle of the CCD camera's field of view is achieved, the maximum tolerable tilt is equal to the depth of focus divided by the field diagonal. Assumptions that a diffraction-limited image quality across the entire field is desired and the optical system has no aberrations except for defocus are made. Tolerable tilt can be controlled by having the scanner comprise a 2-axis tilt stage on which the peg or peg plate is mounted according to an embodiment of the invention.

In another non-limiting embodiment, probe array 140 can be mounted on a 3-axis translation stage (for example, Deltron Precision Inc, Bethel Conn., model LS2-1-A05-XYZ-E-NPN-1). Other suitable translation stages are available from companies such as THK America Inc., Schaumburg, Ill. and IKO International Inc, Torrance, Calif. The X and Y axes of translation are parallel to the plane of probe array 140 and are required if the synthesis area of probe array 140 is larger than the field of view of the detector 390. The Z axis is parallel to the optical axis of lens 350 (perpendicular to the plane of probe array 140) and is used for focus adjustment (for example, see FIG. 3). Each axis may be driven by a stepping motor, for example, a size 14 stepping motor having a step size of 0.9 degrees (Lin Engineering, Santa Clara Calif., model 3509V-03-01), though other motors may be used. The motors are controlled by a 3-axis motion controller (for example, SimpleStep LLC, Newton N.J., model SSXYZMicro77). Leadscrew pitch may be 0.05 inches, for example, and the motors may be driven in microstepping mode with 8 microsteps per full step (3,200 microsteps per revolution). Therefore the size of each microstep is nominally 0.396875 microns. The degrees of freedom are 2 axes of tilt plus one axis of translation (the translation axis can be used for focus adjustment—alternatively, the instrument's main Z stage can be used for focus adjustment). The tilt stage can be, for example, a kinematic tilt stage with 2 stepping-motor-driven actuators (not 3), a tilt stage with piezoelectric actuators instead of stepping motors, a flexure tilt stage, a gimbal stage, a hexapod, or 2 orthogonal goniometers. Examples of motors to drive the tilt stage are, for example, conventional stepping motors, miniature stepping motors (MicroMo Electronics Inc, Clearwater Fla.), servo motors, linear motors or piezoelectric actuators. The translation stages can optionally include linear or rotary encoders. Alternatively, probe array 140 can be mounted on a two-axis (XY) stage and lens 350 can be mounted on a single-axis (Z) stage. The Z axis can be vertical, horizontal, or at some other angle.

The 3-axis translation stage might not be necessary. The Z axis (and the autofocus process) can be omitted if mechanical tolerances in packaging and mounting probe array 140 are sufficiently tight. The X and Y axes can be omitted if probe array 140 is smaller than the field of view of the detector 390.

Filter Wheel/Filter Slider

Figure 8:
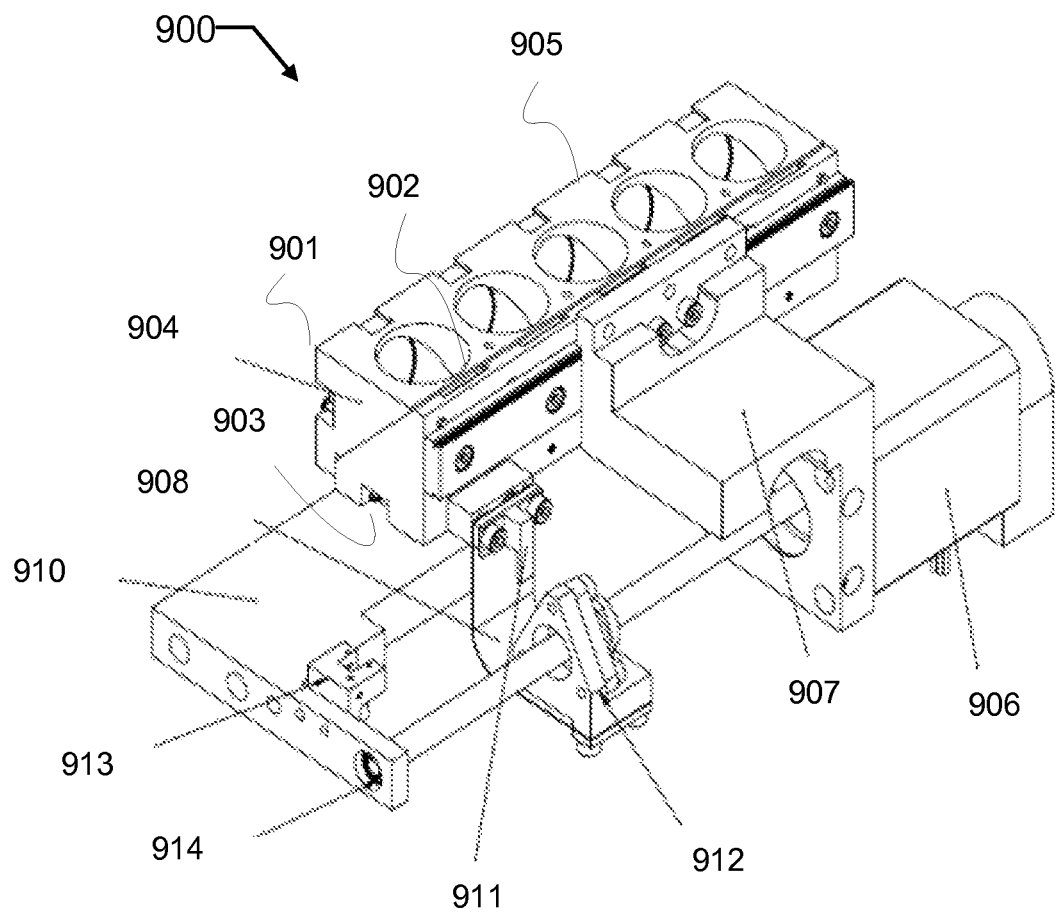
FIG. 8 illustrates a filter slider assembly according to an embodiment of the present invention.

According to an embodiment of the present invention, an example of a filter slider 900 is provided as shown in FIG. 8. The target molecules can be labeled with light-scattering particles (for example, gold or silver nanoparticles with diameters in the range of approximately 1 to 100 nanometers) or with phosphorescent labels instead of fluorescent labels. Filter 360 can be replaced by two or more filters (having different transmission spectra) mounted on a manual or motorized filter wheel or filter slider. The instrument can then be used to sequentially obtain two-color or multi-color, for example, 4 color (or 1-, 2-, or 3-color) fluorescence images of the array to which has been hybridized labeled sample nucleic acid, which can be useful if the target molecules hybridized to probe array 140 are labeled with two or more different fluorophores. For example, if target molecules are labeled with four different semiconductor nanocrystal labels having peak emission wavelengths of 565 nm, 605 nm, 655 nm, and 705 nm, suitable emission filters include Chroma models HQ565/40, HQ605/40, HQ655/40, and HQ705/40 respectively. In a further embodiment, biotin-streptavidin-phycoerythrin and fluorescein-antifluorescein-allophycocyanin or biotin-streptavidin-allophycocyanin and fluorescein-antifluorescein-phycoerythrin are used. The instrument can be used to simultaneously obtain two-color or multi-color images if it contains two or more cameras. For each color there can be a filter set containing an excitation filter 901, a beamsplitter 902, and an emission filter 903. Either the excitation filter 901 or the emission filter 903 or both filters can be omitted with a filter set. The beamsplitter 902 can be either a dichroic beamsplitter or a neutral-density filter. The 5 (or fewer) filter sets are mounted in a filter block 904 that is mounted on a linear slide 905. The linear slide 905, for example, a recirculating ball slide manufactured by THK or IKO, is driven by a linear actuator 906 manufactured by, for example, HaydonKerk Motion Solutions, Waterbury, Conn. The linear slide is connected to the linear actuator by a slide bracket 907. The linear actuator 906 can include a stepping motor, a leadscrew, and a leadscrew nut. The linear actuator 906 is coupled to the linear slide 905 using a slider blade 908, for example, a thin piece of steel shim stock bent into an L shape. This couple is sufficiently flexible so that the filter slider functions properly even if the linear actuator is angularly or laterally misaligned relative to the linear slide. An EOT flag 911 can be installed and a nut bracket 912 can be used to couple the slider bade to the actuator. The support arm 910 can be mounted to the chassis of the instrument. An amplified photo microsensor 913 and a deep groove ball bearing 914 is attached to the support arm.

Probe array 140 does not need to be a DNA array. It could be a peptide array or some other type of array. The instrument described above can scan an array on a peg, array on a peg strip, array on a plate, etc. (See U.S. patent application Ser. No. 11/243,621 which is hereby incorporated by reference herein in its entirely for all purposes).

An additional example of a scanner system with a similar optical architecture is described in U.S. patent application Ser. No. 11/379,641, titled "Methods and Devices for Reading Microarray", filed Apr. 22, 2005 which is hereby incorporated by reference herein in its entirety for all purposes.

In an additional embodiment, disclosed is a method of manufacturing a filter slider for reading a biological array. A linear slide and a plurality of filter sets are provided (See FIG. 8). The filter sets are mounted in a fixture that is mounted on a linear slide. A linear actuator is also provided and coupled to the linear slide such that the filer slider functions properly even if the linear actuator is misaligned relative to the linear slide. The linear actuator comprises a motor. In an alternate embodiment, the motor is a stepping motor and a blade slider, such as a steel shim stock couples the linear actuator with the filter slider.

Autofocusing

The plane of probe array 140 is usually not exactly parallel to the XY plane of the translation stages because of mechanical tolerances in packaging probe array 140 and mounting probe array 140 on the instrument. Therefore, optimum focus can be different for each sub-array. Each corner sub-array can contain at least one reflective feature, for example, a chrome square or L such as reflective feature 405. In one embodiment, a corner sub-array is illuminated by the 590-nm LED, and images are taken as focus is adjusted in 1-micron to 10-micron steps. Sharpness is calculated for each image. Sharpness at other Z positions can be calculated by quadratic interpolation (parabola fitting). The sub-array is in best focus when the calculated sharpness is a maximum. This process is performed for each of the corner sub-arrays before any of the fluorescence images are taken. Optimum focus for the other sub-arrays may be interpolated.

According to a embodiment, a method to image a probe array is provided. A plurality of fiducials on the surface of the probe array is used to improve the image flatness of the surface image. A plurality of images is taken with a camera at a plurality of different z positions. The sharpness at each z position is determined by using one or more image software program. A best z position is chosen by comparing the images of the various z positions and choosing the sharpest image. The above steps are repeated until the best z position of each fiducial on the probe array are determined. The data are transmitted to a computer, wherein the computer includes a surface fitting algorithm. A surface fit profile is calculated on the computer employing the surface fitting algorithm and the transmitted measurement data. Based on the calculations of the surface fit profile, one or more surface non-flatness parameters can be adjusted to improve the image flatness of the surface image of the probe array.

In alternate embodiments, the imaging method may include a number of fiducials, for example, at least 4, at least 5 and at least 9 fiducials. The surface fitting algorithm may include a least square, sub-plane surface fit, and B spline surface fit.

In another embodiment, the imaging method includes the array on a tilt stage which is discussed later in the application. The focusing includes tilting the tilt stage so that the array surface is made parallel to a focal plane of a microscope objective.

In a further embodiment, the surface non-flatness parameters include an array tilt, stage movement effect and optical parameters. In another embodiment, the surface non-flatness parameter, a focal plane is adjusted by moving a lens.

These methods may be applicable in many different systems, globally, across the field of microarray analysis. Having described various embodiments and implementations, it should be apparent to those skilled in the relevant art that the foregoing embodiments are merely illustrative and not limiting, having only been presented by way of example. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements showed as distinct for purposes of illustration may be incorporated within other functional elements in a particular implementation. Also, the sequencing of functions or portions of functions generally may be altered. Certain functional elements, files, data structures, and so on may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

Figure 4B:
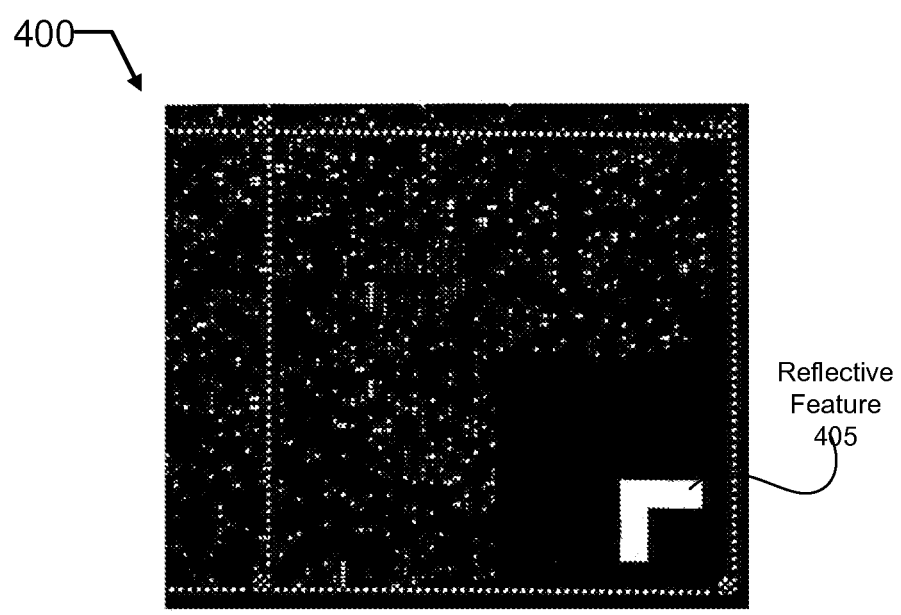

In another non-limiting embodiment, the reflected-light images can also be used to adjust the position of probe array 140 in the X and Y directions to ensure that each sub-array is centered in the field of view of the detector 390, because the positions of the chrome features relative to the fluorescent features can be known, for example, the chrome features shown in FIGS. 4A and 4B. The chrome features can be in various substrates which are understood for one skilled in the art in various applications, for example, biological, biotechnology, medical diagnostics, chemical reactions, and the like. FIGS. 4A and 4B are images of corner sub-arrays 400 taken with both 530-nm excitation (for fluorescence imaging) and 590-nm excitation (for reflected-light imaging), respectively. The small square features are fluorescently labeled. The large L-shaped feature is a chrome mark, illustrated as reflective feature 405 that is used for autofocusing. The surface profile of an array is a larger factor as one goes to smaller feature sizes. Factors that cause a non-flat surface include, for example, a tilt (how parallel the array surface is to the scanner focus plane), stage movement effect (flatness and thread), array surface roughness, and optical parameters. Many other methods and arrangements of autofocus features are possible as described in the following non-limiting examples. In these examples, a fiducial is located at the center of each subarray.

Figure 5A:
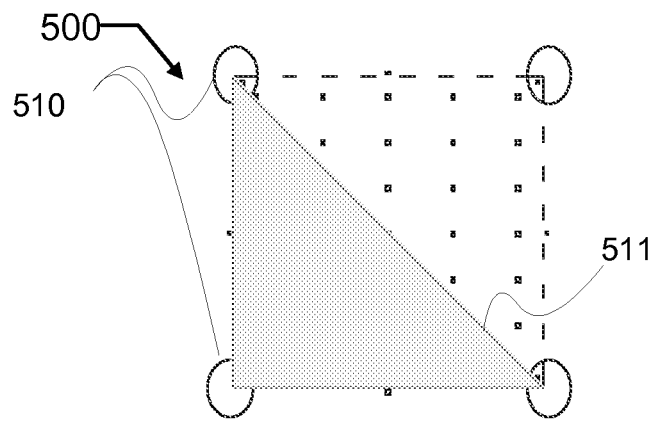
FIGS. 5A, 5B, and 5C illustrate a 4-point auto-focusing method according to an embodiment of the present invention.
Figure 5B:
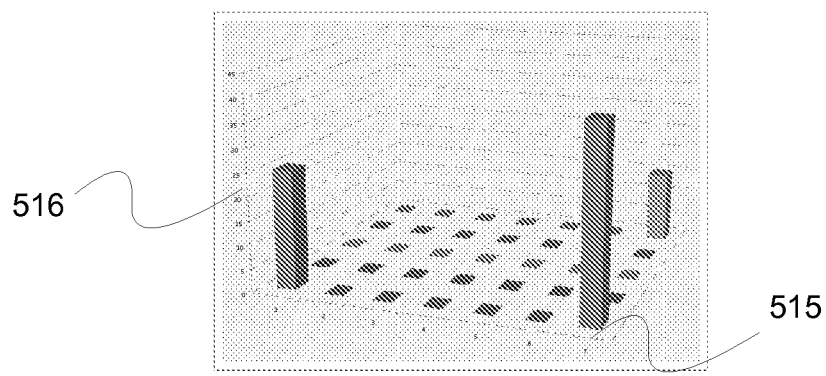
Figure 5C:
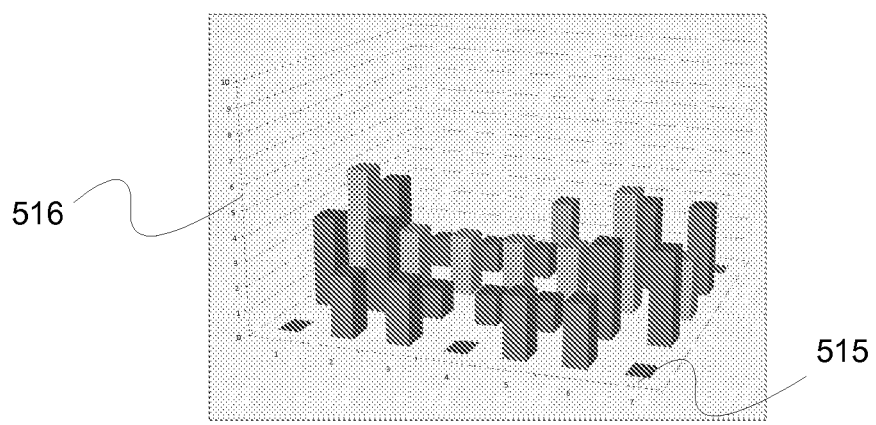

According to one embodiment, autofocus features or fiduciaries are located near the four corners of probe array 140 in the 4-point analysis. The number of points and locations of the fiducials (510) on an array 500 that are measured for the 4-point analysis are indicated in FIG. 5A. The shape of each plane 511 that is being analyzed is also indicated in FIG. 5A. FIG. 5B shows a scanned image of the results from the 4 points array surface analysis. The factors that cause a non-flat surface, for example, a focal plane, can be adjusted. FIG. 5C shows a comparison of a characterization of the array surface between the "calculated" surface and the actual surface. The X axis 515 displays the location on the array and the Y axis 516 displays the relative height to the lowest corner. According to an embodiment, additional autofocus features or fiducials are used to calculate the array surface profile.

Figure 6A:
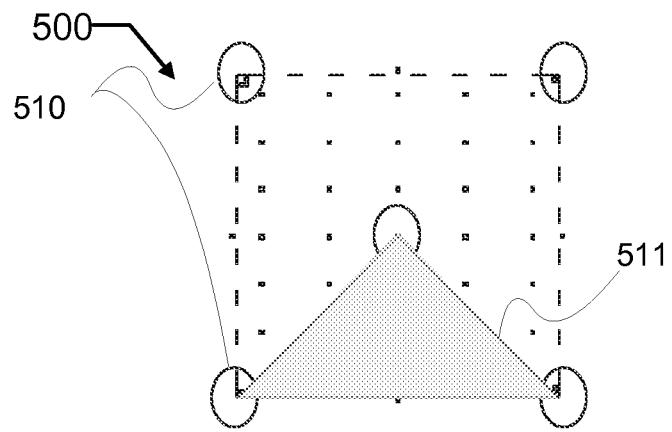
FIGS. 6A, 6B, and 6C illustrate a 5-point auto-focusing method according to another embodiment of the present invention.
Figure 6B:
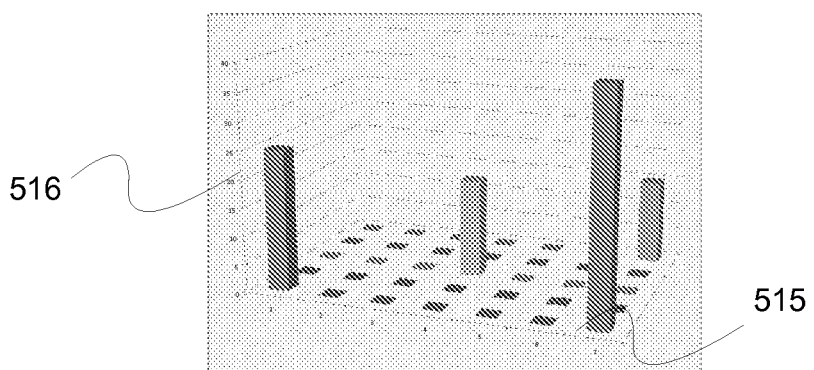
Figure 6C:
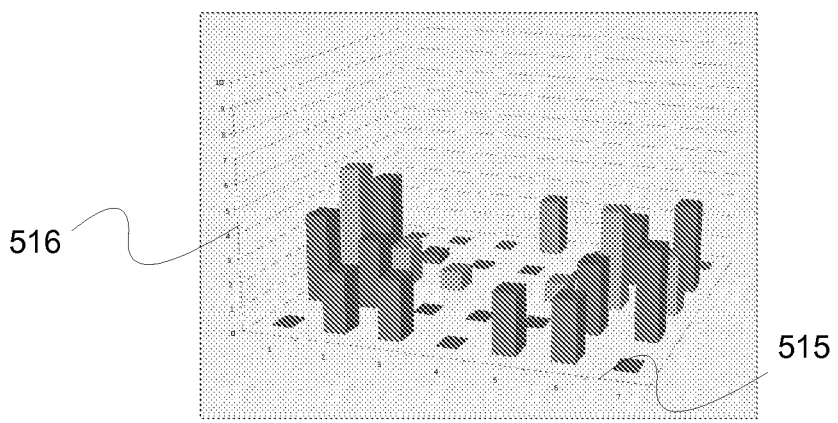

FIGS. 6A, 6B, and 6C illustrate a 5-point auto-focusing method according to another embodiment of the present invention. The number of points and locations of the fiducials (510) on an array 500 that are measured for the 5-point analysis are indicated in FIG. 6A. The shape of each plane 511 that is being analyzed is also indicated in FIG. 6A. FIG. 6B shows a scanned image of the results from the 5 points array surface analysis. Auto focusing is performed to the four corners and a center mark. The tilt is adjusted and small compensations of stage movement are made. FIG. 6C shows the comparison of the characterization of the array surface between the "calculated" surface of the 5 point auto focusing method and the actual surface.

Figure 7A:
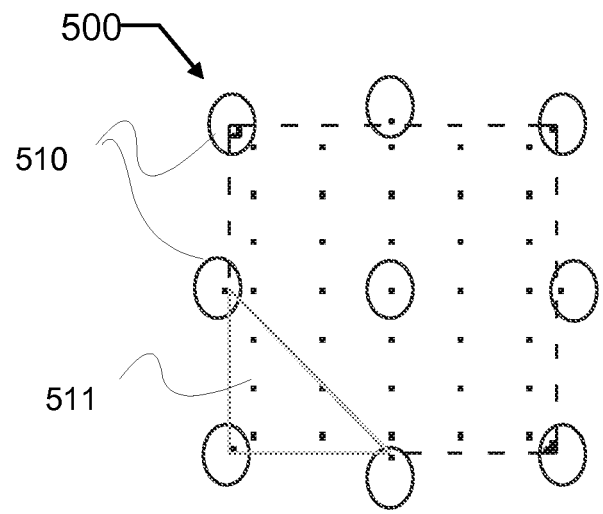
FIGS. 7A, 7B, 7C, 7D and 7E illustrate a 9-point auto-focusing method according to a further embodiment of the present invention.
Figure 7B:
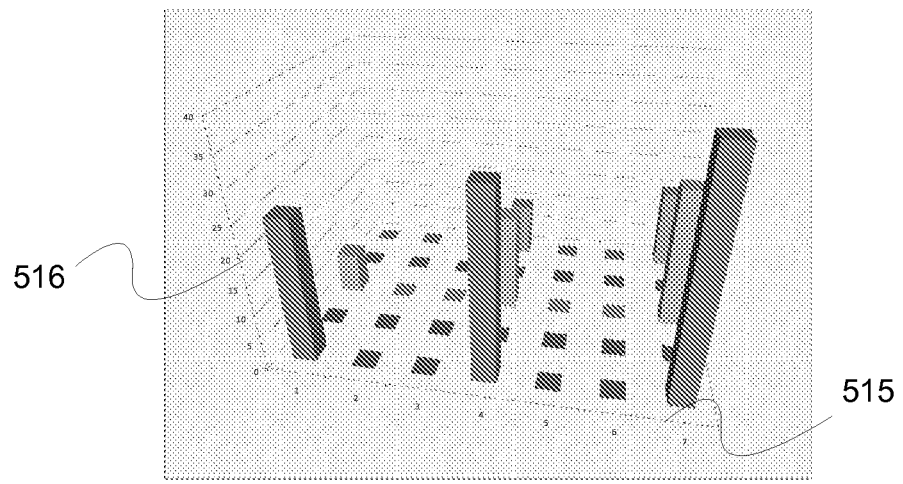
Figure 7C:
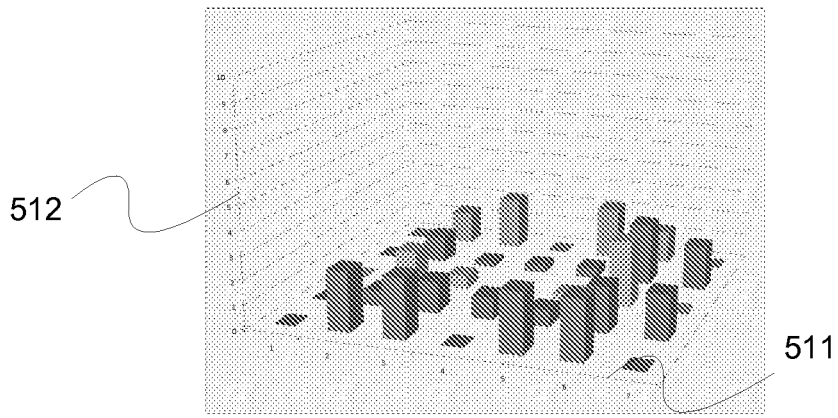
Figure 7D:
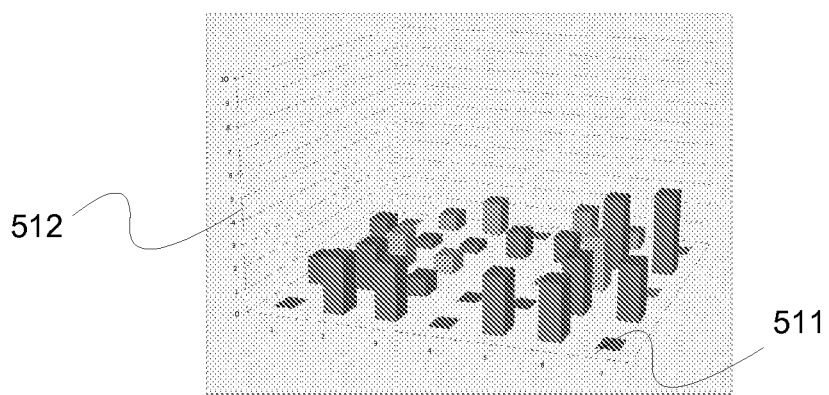
Figure 7E:
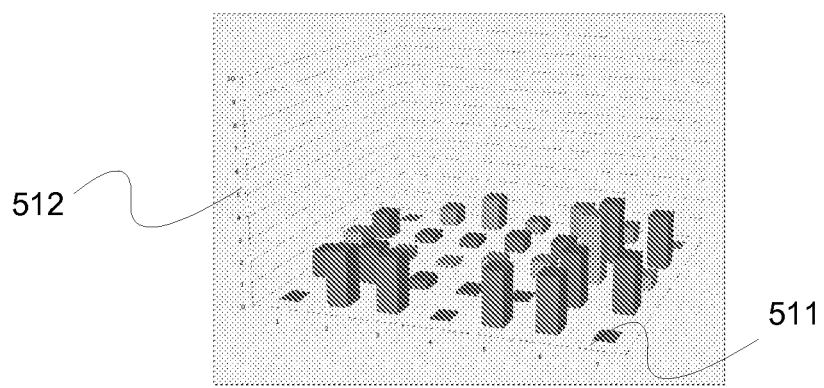

FIGS. 7A, 7B, 7C, 7D and 7E illustrate a 9-point auto-focusing method according to a further embodiment of the invention. The number of points and locations of the fiducials (510) on an array 500 that are measured for the 9-point analysis are indicated in FIG. 7A. The shape of each plane 511 that is being analyzed is also indicated in FIG. 7A. FIG. 7B shows a scanned image of the results from the 9 points analysis. By performing the 9 point analysis with a surface fitting algorithm, the tilt can be adjusted and compensations for stage movement and for the array surface roughness can be made. Various surface fitting algorithms are known in the art, for example, least square, sub-plane surface fit, and the B spline surface fit. FIGS. 7C, 7D, and 7E show the comparisons of the characterization of the array surface between the "calculated" and the actual surface by using these surface fitting algorithms. FIG. 7C shows the results from using the least square algorithm, where the best fit plane is determined by using the nine measurements with the assumption that the array surface is linear. The sub-plane surface fit algorithm includes dividing the array surface into small sub-planes and using multiple planes to describe the array surface. FIG. 7D shows the results from using the sub-plane surface fit algorithm. The assumption that the array surface is smooth and curved is made when using the B spline surface fit algorithm. The results from using the B spline surface fit algorithm are shown in FIG. 7E.

Many other arrangements of autofocus features are possible as described in the following non-limiting examples.

For example, autofocus features can be located near three corners of probe array 140, or in three non-collinear locations that are not corners. Alternatively, a single autofocus feature may be located near the middle of probe array 140, and the other autofocus features may be absent. As another alternative, every one of the sub-arrays might contain one or several autofocus features (for example, 1, 3, 5, 9, 12, 15, etc). The number of autofocus features and locations will depend on factors such a shape of a probe array, number of subarrays, feature size, throughput requirements, stage accuracy, depth of focus of the optics, etc.

In addition to several different arrangements of autofocus features, there are also several other autofocus methods that are possible. For example, source 320B can be omitted, and source 320A can be used to obtain images of the reflective features for purposes of finding focus. In this case, filter 360 is mounted on a motorized slider or filter wheel and is removed from the optical path during the autofocus process (because filter 360 has no transmission at the emission wavelengths of source 320A). Alternatively, the reflective features can be omitted, and autofocus can be performed by taking a series of fluorescence images. This method is undesirable if the fluorophores are susceptible to photobleaching. As another alternative, the features used for autofocusing can be polyimide rather than chrome.

Additional examples of reflective elements and methods such as the parabola fit employed for auto-focus are described in U.S. patent application Ser. No. 10/389,194, titled "System, Method and Product for Scanning of Biological Materials", filed Mar. 14, 2003; and U.S. patent application Ser. No. 10/769,575, titled "System and Method for Calibration and Focusing a Scanner Instrument Using Elements Associated with a Biological Probe Array", filed Jan. 29, 2004; both of which are hereby incorporated by reference herein in its entirety for all purposes.

In some embodiments, the autofocus methods described in U.S. Pat. Nos. 5,578,832 and 5,631,734, both of which are hereby incorporated by reference herein it their entireties for all purposes, may be employed instead of the autofocus methods described above.

According to an embodiment of the present invention, a method to increase the speed of autofocusing is provided. A CCD readout speed is, for example, 20 million pixels per second. According to an embodiment, a method to speed up the autofocus is provided. Instead of reading out, for example, all 2048×2048 pixels from the CCD, a region of interest can be defined on the CCD and only the pixels from the region of interest can then be read. In an alternative embodiment of the present invention, the method comprises binning pixels in groups of for example, 2×2, and reading out the binned pixels instead of the individual pixels.

Many variations of the instrument described above are possible. Some of these variations are listed below. The instrument can hold several probe arrays and scan them sequentially. The instrument can scan a well plate, for example, a 96-well plate, a 384-well plate, etc., if the translation stages have sufficient travel. The positions of source 320A and source 320B can be switched. In this case, beamsplitter 340 can be a shortpass dichroic beamsplitter instead of a longpass dichroic beamsplitter. One or both LEDs can be replaced by sources such as a plurality of LED (i.e. greater than two LEDs), a white light LED, a solid state light source (Lumen Corp, San Diego, Calif.), an arc lamp, a flash lamp, a metal-halide lamp, or a laser.

Abbe illumination can be used instead of Kohler illumination. If Abbe illumination is used, it might be desirable to homogenize the light from source 320A by means of a rectangular light pipe or, light tunnel, or randomizing fiber-optic bundle, with the exit face of the homogenizer being imaged onto probe array 140.

If lens 350 has a sufficiently long working distance, light from source 320A can bypass lens 350 and strike probe array 140 at an angle of incidence of approximately 45 degrees. In this case, it might be desirable to use several LEDs surrounding lens 350 for fluorescence excitation instead of a single LED.

A mirror can be used to introduce a 90-degree bend in the optical path between beamsplitter 340' and exit pupil 343, or between beamsplitter 340' and filter 360, or between lens 370 and the detector 390. This 90-degree bend might make the optical system more compact.

The focal lengths and focal-length ratios of lenses 323A, 323B, and 329 can be changed. Lens 370 can be a commercially available camera lens or a custom multi-element lens. Lens 350 can be a single-element or multi-element lens that is not a microscope objective. Lens 350 can be a finite-conjugate rather than an infinite-conjugate objective; in this case, lens 370 can be omitted.

Cameras having a larger or smaller number of pixels and larger or smaller pixel sizes can be used. Cameras with 4.19 million light-sensitive pixels (2048×2048) are available from several manufacturers including Apogee Instruments Inc (Roseville Calif., model U4000) and Roper Scientific Inc (Tucson Ariz., model K4); the pixel size for these cameras is 7.4 microns×7.4 microns. Cameras with 11 million light-sensitive pixels are available also. The camera can have 8, 10, 12, 14, or 16-bit digital output and can use a USB (universal serial bus), IEEE-1394 (FireWire), or PCI interface. Alternatively, the camera can have analog output that is digitized by a frame grabber. The camera can contain a CMOS sensor rather than a CCD sensor. In some cases, a very inexpensive consumer-grade camera might be usable.

C. Applications Using Nucleic Acid Arrays

A variety of applications using nucleic acid arrays are described in U.S. Pat. No. 7,005,259, which is hereby incorporated herein by reference in its entirety for all purposes.

The methods and compositions described herein may be used in a range of applications including biomedical and genetic research as well as clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839. The nucleic acid arrays may be used in many other applications including detection of genetic diseases such as cystic fibrosis, diabetes, and acquired diseases such as cancer, as disclosed in U.S. patent application Ser. No. 08/143,312 (abandoned). Genetic mutations may be detected by sequencing by hybridization. In one embodiment, genetic markers may be sequenced and mapped using Type-IIs restriction endonucleases as disclosed in U.S. Pat. No. 5,710,000.

Other applications include chip based genotyping, species identification and phenotypic characterization, as described in U.S. Pat. No. 6,228,575, filed Feb. 7, 1997, and U.S. application Ser. No. 08/629,031 (abandoned), filed Apr. 8, 1996. Still other applications are described in U.S. Pat. No. 5,800,992.

Gene expression may be monitored by hybridization of large numbers of mRNAs in parallel using high density arrays of nucleic acids in cells, such as in microorganisms such as yeast, as described in Lockhart et al., Nature Biotechnology, 14:1675 1680 (1996). Bacterial transcript imaging by hybridization of total RNA to nucleic acid arrays may be conducted as described in Saizieu et al., Nature Biotechnology, 16:45 48 (1998). Accessing genetic information using high density DNA arrays is further described in Chee, Science 274:610 614 (1996).

Still other methods for screening target molecules for specific binding to arrays of polymers, such as nucleic acids, immobilized on a solid substrate, are disclosed, for example, in U.S. Pat. No. 5,510,270.

Devices for concurrently processing multiple biological chip assays are useful for each of the applications described above (See, for example, U.S. Pat. No. 5,545,531). Methods and systems for detecting a labeled marker on a sample on a solid support, wherein the labeled material emits radiation at a wavelength that is different from the excitation wavelength, which radiation is collected by collection optics and imaged onto a detector which generates an image of the sample, are disclosed in, for example, U.S. Pat. No. 5,578,832. These methods permit a highly sensitive and resolved image to be obtained at high speed. Methods and apparatus for detection of fluorescently labeled materials are further described in U.S. Pat. Nos. 5,631,734 and 5,324,633.

Typically, in carrying out these methods, the housed substrate is mounted on a hybridization station where it is connected to a fluid delivery system. After hybridization, a rinsing/washing step occurs. Following hybridization and appropriate rinsing/washing, the housed substrate may be aligned on a detection or imaging system. Descriptions of these steps are described in detail in U.S. Pat. No. 5,959,098, which is hereby incorporated herein by reference in its entirety for all purposes.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method for improving image flatness of a surface image of a probe array having an array surface roughness, the method comprising:
    imaging one or more fiducials of the probe array and determining a position measurement for each of the one or more fiducials based on at least image sharpness;
    generating a surface fit profile based on one or more of the position measurements; and
    imaging the probe array and adjusting one or more surface non-flatness parameters based on the surface fit profile to improve the image flatness of the surface image of the probe array.

2. The method of claim 1, wherein the one or more fiducials are imaged at one or more positions along an axis of translation.

3. The method of claim 1, wherein the surface fit profile is generated using a surface-fitting algorithm.

4. The method of claim 3, wherein the surface-fitting algorithm comprises at least one of a least square algorithm, a sub-plane surface fit algorithm, and a B spline surface fit.

5. The method of 1, wherein determining the position measurement comprises using quadratic interpolation for at least one of the one or more fiducials.

6. The method of claim 1, wherein the one or more surface non-flatness parameters comprises a probe array tilt angle.

7. The method of claim 6, wherein adjusting the one or more surface non-flatness parameters comprises adjusting a position of a stage on which the probe array is mounted.

8. The method of claim 7, wherein the stage comprises a two-axis tilt stage.

9. The method of claim 7, wherein the stage comprises a three-axis translation stage.

10. The method of claim 1, wherein the one or more surface non-flatness parameters comprise an optical parameter.

11. The method of claim 1, wherein the one or more surface non-flatness parameters comprise a focal plane position.

12. The method of claim 1, wherein the one or more fiducials comprise at least 4 fiducials.

13. The method of claim 12, wherein the one or more fiducials comprise at least 5 fiducials.

14. The method of claim 13, wherein the one or more fiducials comprise at least 9 fiducials.

15. The method of claim 14, wherein the one or more fiducials comprise 12 fiducials.

16. The method of claim 15, wherein the one or more fiducials comprise 15 fiducials.

17. The method of claim 1, wherein the axis of translation is substantially perpendicular to a plane of the probe array.

18. The method of claim 1, wherein imaging the one or more fiducials comprises adjusting a position of a stage on which the probe array is mounted.

19. The method of claim 1, wherein the probe array comprises a DNA array.

20. The method of claim 1, wherein the probe array comprises a peptide array.

21. The method of claim 1, wherein the probe array comprises a plurality of sub-arrays.

22. The method of claim 21, wherein the one or more fiducials are of a corner sub-array of the probe array.

23. The method of claim 21, wherein the probe array is positioned such that a selected sub-array is centered in a field of view of an image detector device.

24. The method of claim 1, wherein the one or more fiducials comprise a plurality of fiducials located in non-collinear locations on the probe array.

25. The method of claim 1, wherein the one or more fiducials comprise one of an L-shaped or square shaped feature.

26. The method of claim 1, wherein at least one of the one or more fiducials is located near a middle of the probe array.

27. A system for improving image flatness of a surface image of a probe array having an array surface roughness, the system comprising:
    an image detector device comprising at least one imaging sensor configured to:
        image one or more fiducials of the probe array and determine a position measurement for each of the one or more fiducials based on at least image sharpness; and
    at least one server coupled with the image detector device, the at least one server comprising a non-transitory computer readable memory and at least one processor and that is, upon execution of software instructions stored in the non-transitory computer readable memory, configured to:
        generate a surface fit profile based on one or more of the position measurements; and facilitate imaging the probe array by adjusting one or more surface non-flatness parameters based on the surface fit profile to improve the image flatness of the surface image of the probe array.

28. A computer program product embedded in a non-transitory computer readable medium comprising instructions executable by a computer processor for improving image flatness of a surface image of a probe array having an array surface roughness, the instructions being executable by a computer processor to execute processing comprising:
  imaging one or more fiducials of the probe array and determining a position measurement for each of the one or more fiducials based on at least image sharpness;
  generating a surface fit profile based on one or more of the position measurements; and
  imaging the probe array and adjusting one or more surface non-flatness parameters based on the surface fit profile to improve the image flatness of the surface image of the probe array.

* * * * *